(12) United States Patent
Tostoes et al.

(10) Patent No.: US 11,459,540 B2
(45) Date of Patent: Oct. 4, 2022

(54) EXPANDED BED AFFINITY SELECTION

(71) Applicant: FloDesign Sonics, Inc., West Springfield, MA (US)

(72) Inventors: Rui Tostoes, Northampton, MA (US); Bart Lipkens, Bloomfield, CT (US); Kedar Chitale, Vernon, CT (US); Benjamin Ross-Johnsrud, Northampton, MA (US); Walter M. Presz, Jr., Wilbraham, MA (US); Jack Saloio, Ludlow, MA (US)

(73) Assignee: FloDesign Sonics, Inc., West Springfield, MA (US)

( * ) Notice: Subject to any disclaimer, the term of this patent is extended or adjusted under 35 U.S.C. 154(b) by 603 days.

(21) Appl. No.: 15/983,823

(22) Filed: May 18, 2018

(65) Prior Publication Data

US 2019/0062690 A1 Feb. 28, 2019

Related U.S. Application Data

(63) Continuation-in-part of application No. 15/963,809, filed on Apr. 26, 2018, and a continuation-in-part of application No. 15/522,800, filed on Jul. 28, 2016.
(Continued)

(51) Int. Cl.
*C12M 1/00* (2006.01)
*C12M 1/42* (2006.01)
(Continued)

(52) U.S. Cl.
CPC ......... *C12M 47/02* (2013.01); *B01D 15/1807* (2013.01); *B01D 15/3809* (2013.01);
(Continued)

(58) Field of Classification Search
CPC ............ G01N 30/76; G01N 33/54313; G01N 30/7293; G01N 30/462; G01N 2030/027;
(Continued)

(56) References Cited

U.S. PATENT DOCUMENTS 2,473,971 A 6/1949 Ross
2,667,944 A 2/1954 Crites
(Continued)

FOREIGN PATENT DOCUMENTS

AU 2002236405 9/2002
CN 105 087 788 A 11/2015
(Continued)

OTHER PUBLICATIONS

Hammarstrom et al. (Lab on Chip, 2012, 12, 4296-4304). (Year: 2012).*
(Continued)

*Primary Examiner* — Brian R Gordon
(74) *Attorney, Agent, or Firm* — FloDesign Sonics, Inc.

(57) ABSTRACT

Separation of materials is achieved using affinity binding and acoustophoretic techniques. A column provided with a fluid mixture of materials for separation and support structures may be used with acoustic waves to block flow of the support structures. The support structures can have an affinity for one or more materials in the fluid mixture. By blocking flow of the support structures, materials bound or adhered to the support structure are also blocked.

20 Claims, 13 Drawing Sheets

Related U.S. Application Data

(60) Provisional application No. 62/508,385, filed on May 18, 2017, provisional application No. 62/490,574, filed on Apr. 26, 2017, provisional application No. 62/197,801, filed on Jul. 28, 2015.

(51) Int. Cl.
  *B01D 15/38* (2006.01)
  *C12N 13/00* (2006.01)
  *B01D 15/18* (2006.01)

(52) U.S. Cl.
  CPC ......... *B01D 15/3866* (2013.01); *C12M 35/04* (2013.01); *C12N 13/00* (2013.01)

(58) Field of Classification Search
  CPC .. C07K 1/22; B01D 15/1807; B01D 15/3823; B01D 15/3866; C12N 13/00; C12M 35/04
  See application file for complete search history.

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,125,789 A | 11/1978 | Van Schoiack |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,484,907 A | 11/1984 | Sheeran, Jr. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,404 A * | 10/1991 | Mansour ............... C02F 11/10 423/201 |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,562,823 A | 10/1996 | Reeves |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,766,947 A * | 6/1998 | Rittershaus ............. A61P 29/00 435/334 |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 6/2000 | Raghavarao et al. |
| 6,166,231 A | 12/2000 | Hoeksema |
| 6,216,538 B1 | 4/2001 | Yasuda et al. |
| 6,221,258 B1 | 4/2001 | Feke et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,674,630 B2 | 3/2010 | Siversson |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |

(56) References Cited

U.S. PATENT DOCUMENTS

| | | |
|---|---|---|
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Cancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliavsky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,810,665 B2 | 11/2017 | Fernald et al. |
| 9,833,763 B2 | 12/2017 | Fernald et al. |
| 9,869,659 B2 | 1/2018 | Buckland et al. |
| 9,872,900 B2 | 1/2018 | Ciaramella et al. |
| 9,873,126 B2 | 1/2018 | Mao et al. |
| 9,873,894 B2 | 1/2018 | Conway et al. |
| 9,878,056 B2 | 1/2018 | Bancel et al. |
| 9,878,536 B2 | 1/2018 | Foresti et al. |
| 9,879,087 B2 | 1/2018 | DeSander et al. |
| 9,990,297 B2 | 1/2018 | Conway et al. |
| 9,907,846 B2 | 3/2018 | Morein et al. |
| 9,909,117 B2 | 3/2018 | Kaduchak |
| 9,909,313 B1 | 3/2018 | Grubbs |
| 9,913,656 B2 | 3/2018 | Stulen |
| 9,913,866 B2 | 3/2018 | O'Shea et al. |
| 9,925,277 B2 | 3/2018 | Almarsson et al. |
| 9,926,382 B2 | 3/2018 | Fischer et al. |
| 9,937,207 B2 | 4/2018 | Gregory et al. |
| 9,938,390 B2 | 4/2018 | Storti et al. |
| 9,943,599 B2 | 4/2018 | Gehlt et al. |
| 9,944,702 B2 | 4/2018 | Galetto |
| 9,944,709 B2 | 4/2018 | Galetto |
| 9,994,743 B2 | 4/2018 | El-Zahab |
| 9,974,898 B2 | 5/2018 | Spain et al. |
| 9,983,459 B2 | 5/2018 | Arnold |
| 10,006,052 B2 | 6/2018 | Jarjour |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0057886 A1 | 3/2004 | Zumeris et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0055136 A1 | 3/2005 | Hofmann et al. |
| 2005/0121269 A1 | 6/2005 | Namduri |
| 2005/0145567 A1 | 7/2005 | Quintel et al. |
| 2005/0196725 A1 | 9/2005 | Fu |
| 2005/0239198 A1 | 10/2005 | Kunas |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0138108 A1 | 6/2007 | Hadfield et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0042253 A1 | 2/2009 | Hiller et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |

(56) References Cited

U.S. PATENT DOCUMENTS

| | | |
|---|---|---|
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0161903 A1 | 6/2012 | Thomas et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0206688 A1 | 8/2013 | El-Naas |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2013/3146412 | 11/2013 | Schultz |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugharn, Jr. et al. |
| 2014/0154795 A1 | 6/2014 | Lipkens et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0274550 A1 | 10/2015 | Lipkens et al. |
| 2015/0321129 A1 | 11/2015 | Lipkens et al. |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot et al. |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0080423 A1 | 3/2017 | Dauson et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Gaietto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper et al. |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |
| 2017/0374730 A1 | 12/2017 | Flores |
| 2018/0000311 A1 | 1/2018 | Lipkens et al. |
| 2018/0000870 A1 | 1/2018 | Britt |
| 2018/0000910 A1 | 1/2018 | Chakraborty et al. |
| 2018/0001011 A1 | 1/2018 | Paschon et al. |
| 2018/0008707 A1 | 1/2018 | Bussmer et al. |
| 2018/0009158 A1 | 1/2018 | Harkness et al. |

(56) References Cited

U.S. PATENT DOCUMENTS

| | | | |
|---|---|---|---|
| 2018/0009888 A9 | 1/2018 | Baumeister et al. |
| 2018/0009895 A1 | 1/2018 | Smith et al. |
| 2018/0010085 A1 | 1/2018 | Lipkens et al. |
| 2018/0014846 A1 | 1/2018 | Rhee |
| 2018/0015128 A1 | 1/2018 | Britt |
| 2018/0015392 A1 | 1/2018 | Lipkens et al. |
| 2018/0016570 A1 | 1/2018 | Lipkens et al. |
| 2018/0016572 A1 | 1/2018 | Tang |
| 2018/0020295 A1 | 1/2018 | Pander et al. |
| 2018/0021379 A1 | 1/2018 | Gaietto et al. |
| 2018/0022798 A1 | 1/2018 | Shurpf et al. |
| 2018/0028683 A1 | 2/2018 | Wong et al. |
| 2018/0043473 A1 | 2/2018 | Helvajian et al. |
| 2018/0049767 A1 | 2/2018 | Gee et al. |
| 2018/0051089 A1 | 2/2018 | Galettto et al. |
| 2018/0051265 A1 | 2/2018 | Cooper |
| 2018/0052095 A1 | 2/2018 | Cumbo et al. |
| 2018/0052147 A1 | 2/2018 | Zeng |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0055997 A1 | 3/2018 | Cabrera et al. |
| 2018/0056095 A1 | 3/2018 | Messerly et al. |
| 2018/0057810 A1 | 3/2018 | Zhang et al. |
| 2018/0058439 A1 | 3/2018 | Locke et al. |
| 2018/0066223 A1 | 3/2018 | Lim |
| 2018/0066224 A1 | 3/2018 | Lipkens et al. |
| 2018/0066242 A1 | 3/2018 | Zhang |
| 2018/0067044 A1 | 3/2018 | Kaduchak et al. |
| 2018/0071363 A1 | 3/2018 | Ghatnekar et al. |
| 2018/0071981 A1 | 3/2018 | Collino et al. |
| 2018/0078268 A1 | 3/2018 | Messerly |
| 2018/0080026 A1 | 3/2018 | Rossi et al. |
| 2018/0085743 A1 | 3/2018 | Yavorsky et al. |
| 2018/0087044 A1 | 3/2018 | Lipkens et al. |
| 2018/0088083 A1 | 3/2018 | Sinha |
| 2018/0092338 A1 | 4/2018 | Hering et al. |
| 2018/0092660 A1 | 4/2018 | Ethicon |
| 2018/0094022 A1 | 4/2018 | Bracewell et al. |
| 2018/0095067 A1 | 4/2018 | Huff et al. |
| 2018/0098785 A1 | 4/2018 | Price et al. |
| 2018/0100134 A1 | 4/2018 | Lim |
| 2018/0100204 A1 | 4/2018 | O'Shea |
| 2018/0010758 A1 | 5/2018 | Vincent et al. |
| 2018/0119174 A1 | 5/2018 | Scharenberg et al. |
| 2018/0130491 A1 | 5/2018 | Mathur |
| 2018/0136167 A1 | 5/2018 | Smith et al. |
| 2018/0143138 A1 | 5/2018 | Shreve et al. |
| 2018/0143167 A1 | 5/2018 | Mziray et al. |
| 2018/0147245 A1 | 5/2018 | O'Shea et al. |
| 2018/0147576 A1 | 5/2018 | Lavieu et al. |
| 2018/0148740 A1 | 5/2018 | Conway et al. |
| 2018/0148763 A1 | 5/2018 | Shimada et al. |
| 2018/0153946 A1 | 6/2018 | Alemany et al. |
| 2018/0155716 A1 | 6/2018 | Zhang et al. |
| 2018/0157107 A1 | 6/2018 | Koyama |
| 2018/0161775 A1 | 6/2018 | Kapur et al. |
| 2018/0177490 A1 | 6/2018 | Shiraishi |
| 2018/0178184 A1 | 6/2018 | Holland |
| 2018/0180610 A1 | 6/2018 | Taha |

FOREIGN PATENT DOCUMENTS

| | | |
|---|---|---|
| CN | 104722106 B | 4/2016 |
| DE | 30 27 433 A1 | 2/1982 |
| DE | 32 18 488 A1 | 11/1983 |
| DE | 196 48 519 A1 | 6/1998 |
| DE | 103 19 467 B3 | 7/2004 |
| DE | 10 2008 006 501 A1 | 9/2008 |
| DE | 10 2014 206 823 A1 | 10/2015 |
| EP | 0 292 470 B1 | 11/1988 |
| EP | 0 167 406 B1 | 7/1991 |
| EP | 0 641 606 | 3/1995 |
| EP | 1 175 931 A1 | 1/2002 |
| EP | 1 254 669 B1 | 11/2002 |
| EP | 1 308 724 A2 | 5/2003 |
| EP | 2 209 545 | 7/2010 |
| EP | 270152 A1 | 1/2018 |
| EP | 2419511 | 1/2018 |
| EP | 3068888 | 1/2018 |
| EP | 3257600 | 1/2018 |
| EP | 3274453 | 1/2018 |
| EP | 3274454 | 1/2018 |
| EP | 3275894 | 1/2018 |
| EP | 278108 | 2/2018 |
| EP | 3279315 | 2/2018 |
| EP | 3286214 | 2/2018 |
| EP | 2289535 | 3/2018 |
| EP | 2545068 | 3/2018 |
| EP | 2675540 | 3/2018 |
| EP | 2750683 | 3/2018 |
| EP | 2796102 | 3/2018 |
| EP | 3066201 | 3/2018 |
| EP | 3066998 | 3/2018 |
| EP | 3107552 | 3/2018 |
| EP | 3288660 | 3/2018 |
| EP | 3288683 | 3/2018 |
| EP | 3289362 | 3/2018 |
| EP | 3291842 | 3/2018 |
| EP | 3291852 | 3/2018 |
| EP | 3292142 | 3/2018 |
| EP | 3292195 | 3/2018 |
| EP | 3292515 | 3/2018 |
| EP | 3294343 | 3/2018 |
| EP | 3294764 | 3/2018 |
| EP | 3294857 | 3/2018 |
| EP | 3294871 | 3/2018 |
| EP | 3294888 | 3/2018 |
| EP | 3294896 | 3/2018 |
| EP | 3296302 | 3/2018 |
| EP | 3297740 | 3/2018 |
| EP | 3298046 | 3/2018 |
| EP | 3164488 | 4/2018 |
| EP | 3301115 | 4/2018 |
| EP | 3302783 | 4/2018 |
| EP | 3302789 | 4/2018 |
| EP | 3303558 | 4/2018 |
| EP | 3306310 | 4/2018 |
| EP | 2675901 | 5/2018 |
| EP | 2956772 | 5/2018 |
| EP | 3323444 | 5/2018 |
| EP | 3324996 | 5/2018 |
| EP | 3327127 | 5/2018 |
| EP | 3337819 | 6/2018 |
| GB | 2 420 510 A | 5/2006 |
| JP | 9-136090 | 5/1997 |
| KR | 1442486 | 9/2014 |
| RU | 2037327 C1 | 6/1995 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 95/01214 A1 | 1/1995 |
| WO | WO 97/34643 | 9/1997 |
| WO | WO 1998/017373 | 4/1998 |
| WO | WO 98/50133 A1 | 11/1998 |
| WO | WO 00/41794 | 7/2000 |
| WO | WO 02/072234 A1 | 9/2002 |
| WO | WO 02/072236 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/130321 | 10/2011 |
| WO | WO 2011/131947 A2 | 10/2011 |
| WO | WO 2011/161463 A2 | 12/2011 |

(56) References Cited

FOREIGN PATENT DOCUMENTS

| | | |
|---|---|---|
| WO | WO 2013/043044 A1 | 3/2013 |
| WO | WO 2013/043297 A1 | 3/2013 |
| WO | WO 2013/049623 A1 | 4/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/035457 | 3/2014 |
| WO | WO 2014/046605 A1 | 3/2014 |
| WO | WO 2014/055219 A2 | 4/2014 |
| WO | WO 2014/124306 A1 | 8/2014 |
| WO | WO 2014/153651 | 10/2014 |
| WO | WO 2014/165177 | 10/2014 |
| WO | WO 2015/006730 | 1/2015 |
| WO | WO 2015/102528 | 7/2015 |
| WO | WO 2016/004398 A2 | 1/2016 |
| WO | WO 2016/124542 | 8/2016 |
| WO | WO 2016/176663 | 11/2016 |
| WO | WO 2016/209082 | 12/2016 |
| WO | WO 2017/011519 | 1/2017 |
| WO | WO 2017/021543 | 2/2017 |
| WO | WO 2017/041102 | 3/2017 |
| WO | 2017/132694 A1 | 8/2017 |
| WO | WO 20174201349 | 11/2017 |
| WO | WO 2017218714 | 12/2017 |
| WO | WO 2018/009894 A1 | 1/2018 |
| WO | WO 2018002036 | 1/2018 |
| WO | WO 2018005873 | 1/2018 |
| WO | WO 2018013558 | 1/2018 |
| WO | WO 2018013629 A1 | 1/2018 |
| WO | WO 2018013840 | 1/2018 |
| WO | WO2018014174 | 1/2018 |
| WO | WO2018015561 | 1/2018 |
| WO | WO 20180011600 | 1/2018 |
| WO | WO2018018958 | 2/2018 |
| WO | WO2018021920 | 2/2018 |
| WO | WO2018022158 | 2/2018 |
| WO | WO 2018022513 | 2/2018 |
| WO | WO2018022619 | 2/2018 |
| WO | WO2018022651 | 2/2018 |
| WO | WO2018022930 | 2/2018 |
| WO | WO2018023114 | 2/2018 |
| WO | WO2018024639 | 2/2018 |
| WO | WO2018026644 | 2/2018 |
| WO | WO2018026941 | 2/2018 |
| WO | WO2018028647 | 2/2018 |
| WO | WO 2018034343 | 2/2018 |
| WO | WO2018034885 | 2/2018 |
| WO | WO 2018035141 | 2/2018 |
| WO | WO 2018035423 | 2/2018 |
| WO | WO20180202691 | 2/2018 |
| WO | WO2018034655 | 3/2018 |
| WO | WO 2018038711 | 3/2018 |
| WO | WO 2018039119 | 3/2018 |
| WO | WO 2018039407 | 3/2018 |
| WO | WO 2018039408 | 3/2018 |
| WO | WO 2018039410 | 3/2018 |
| WO | WO 2018039412 | 3/2018 |
| WO | WO 2018039515 | 3/2018 |
| WO | WO 2018045284 | 3/2018 |
| WO | WO 2018049226 | 3/2018 |
| WO | WO 2018050738 | 3/2018 |
| WO | WO 2018057825 | 3/2018 |
| WO | WO 2018063291 | 4/2018 |
| WO | WO 2018058275 | 5/2018 |
| WO | WO 2018081476 | 5/2018 |
| WO | WO 2018091879 | 5/2018 |
| WO | WO2018094244 | 5/2018 |
| WO | WO 20180814701 | 5/2018 |
| WO | WO 2018098671 | 6/2018 |
| WO | WO 2018102752 | 6/2018 |
| WO | WO 2018106163 | 6/2018 |
| WO | WO 2018112145 | 6/2018 |
| WO | WO 2018112335 | 6/2018 |

OTHER PUBLICATIONS

Chromatogrpahy forum re: column volume discussion (Year: 2013).*
Hoke (Infection and Immunity, May 2008, p. 2063-2069 (Year: 2008).*
U.S. Appl. No. 99/908,288, filed Mar. 2018, Harkness.
Alvarez et al.; ShockWaves, vol. 17, No. 6, pp. 441-447, 2008.
Augustsson et al., Acoustophoretic microfluidic chip for sequential elution of surface bound molecules from beads or cells, Biomicrofluidics, Sep. 2012, 6(3):34115.
Benes et al.; Ultrasonic Separation of Suspended Particles, 2001 IEEE Ultrasonics Symposium; Oct. 7-10, 2001; pp. 649-659; Atlanta, Georgia.
Castilho et al.; Animal Cell Technology: From Biopharmaceuticals to Gene Therapy; 11—Animal Cell Separation; 2008.
Castro; Tunable gap and quantum quench dynamics in bilayer graphene; Jul. 13, 2010; Mathematica Summer School.
Chitale et al.; Understanding the Fluid Dynamics Associated with Macro Scale Ultrasonic Separators; Proceedings of Meetings on Acoustics, May 2015.
Cravotto et al.; Ultrasonics Sonochemistry, vol. 15, No. 5, pp. 898-902, 2008.
Garcia-Lopez, et al.; Enhanced Acoustic Separation of Oil-Water Emulsion in Resonant Cavities. The Open Acoustics Journal. 2008, vol. 1, pp. 66-71.
Grenvall et al.; Concurrent Isolation of Lymphocytes and Granulocytes Using Prefocused Free Flow Acoustophoresis; Analytical Chemistry; vol. 87; pp. 5596-5604; 2015.
Higginson et al.; Tunable optics derived from nonlinear acoustic effects; Journal of Applied Physics; vol. 95; No. 10; pp. 5896-5904; 2004.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; Separation of bacterial spores from flowering water in macro-scale cavities by ultrasonic standing waves; submitted/uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et al.; An Industrial-Prototype Acoustic Array for Real-Time Emulsion Layer Detection in Oil Storage Tanks; IEEE Sensors Journal, vol. 9, No. 12, Dec. 2009.

(56) References Cited

OTHER PUBLICATIONS

Musiak et al.; Design of a Control System for Acoustophoretic Separation, 2013 IEEE 56$^{th}$ International Midwest Symposium on Circuits and Systems (MWSCAS), Aug. 2013, pp. 1120-1123.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Phys. Org. "Engineers develop revolutionary nanotech water desalination membrane." Nov. 6, 2006. http://phys.org/news82047372.html.
Ponomarenko et al.; Density of states and zero Landau level probed through capacitance of graphene; Nature Nanotechnology Letters, Jul. 5, 2009; DOI: 10.1038/NNANO.2009.177.
"Proceedings of the Acoustics 2012 Nantes Conference," Apr. 23-27, 2012, Nantes, France, pp. 278-282.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al., J. Chem. Edu., 1990, 67(9), p. 763, published Sep. 1990.
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-196; 2012.
Annex to Form PCT/ISA/206—Communication Relating to the Results of the Partial International Search Report dated Jul. 18, 2013.
European Search Report of European Application No. 11769474.5 dated Sep. 5, 2013.
European Search Report of European Application No. 11796470.0 dated Jan. 5, 2016.
European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.
International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/050729 dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.
International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index.html>.
International Search Report and Written Opinion for International Application No. PCT/US2017/031425 dated Oct. 23, 2017.
International Search Report and Written Opinion for International Application No. PCT/US2018/026617, dated Jul. 4, 2018.
International Search Report and Written Opinion for International Application No. PCT/US2018/31267, dated Aug. 1, 2018.
Jin Zuwei, "Expanded Bed Absorption-Challenges and Advances in Column and Process Design", Pharmaceutical Engineering, vol. 35 No. 1, Jan./Feb. 2015, 12 pages.
Office Action received for European Patent Application No. 18724088.2 dated Feb. 22, 2021, 5 pages.

* cited by examiner

EXPANDED BED AFFINITY SELECTION

CLAIM OF PRIORITY

This application is a continuation-in-part application of and claims priority to U.S. patent application Ser. No. 15/963,809, filed on Apr. 26, 2018, which claims the benefit of U.S. Patent Application Ser. No. 62/490,574, filed on Apr. 26, 2017. This application is also a continuation-in-part application of and claims priority to U.S. patent application Ser. No. 15/222,800, filed on Jul. 28, 2016, which claims the benefit of U.S. Patent Application Ser. No. 62/197,801, filed on Jul. 28, 2015. The entire contents of each of the above applications is hereby incorporated herein by reference.

BACKGROUND

Separation of biomaterial has been applied in a variety of contexts. For example, separation techniques for separating proteins from other biomaterials are used in a number of analytical processes.

Acoustophoresis is a technique for separating particles and/or secondary fluids from a primary or host fluid using acoustics, such as acoustic standing waves. Acoustic standing waves can exert forces on particles in a fluid when there is a differential in density and/or compressibility, known as the acoustic contrast factor. The pressure profile in a standing wave contains areas of local minimum pressure amplitudes at standing wave nodes and local maxima at standing wave anti-nodes. Depending on their density and compressibility, the particles can be driven to and trapped at the nodes or anti-nodes of the standing wave. Generally, the higher the frequency of the standing wave, the smaller the particles that can be trapped.

SUMMARY

This disclosure describes technologies relating to methods, systems, and apparatus for acoustic separation of materials. The materials being separated may be biomaterials. The separation may employ material support structures. The support structures may be beads. A functionalized material may be applied to the support structures that has an affinity for one or more materials to be separated. The support structures may be mixed in a fluid that contains the materials. The fluid mixture may be provided to a fluid column or flow chamber. The support structures can be retained in the column against a fluid or fluid mixture flow through the column by provision of an acoustic standing wave at one end of the column that can prevent the support structures from passing.

In accordance with some examples, an acoustic affinity system is implemented that can include the features of being closed, automated and/or single-use. The system can be considered closed if the components can be sealed from an open-air environment. An automated system is able to operate autonomously, with little or no operator intervention. The system is single use when components and materials employed for an affinity separation run, which may include multiple recirculations, are disconnected and discarded after an affinity separation run. A single use system can avoid the additional steps of cleaning and sterilizing the equipment components and materials for subsequent runs.

In some examples, methods, systems, and apparatuses are disclosed for separation of biomaterials accomplished by functionalized material distributed in a fluid chamber that bind the specific target materials. The specific target materials can be particles, including cells, recombinant proteins and/or monoclonal antibodies. The functionalized material, which may be beads and/or microcarrier structures are coated or otherwise provided with an affinity material for attracting and binding the specific target materials. The affinity material may be a protein, ligand or other material that can form a bond with the target material.

In some example implementations, the affinity material and the target material can form antigen-antibody interactions with binding sites on the functionalized material. In some instances, the target material become bound to the functionalized material when a ligand of the target material or the functionalized material is conjugated to a matrix on the complementary material. The functionalized material includes functionalized microbeads. The functionalized microbeads include a particular antigen ligand that has affinity for a corresponding antibody.

In some examples, material adhered to the support structures with the functionalized material remains in the column, while other free material in the fluid may pass through the acoustic standing wave to provide separation of materials. The support structures may be implemented to have a certain acoustic contrast factor based on their density, compressibility, size or other characteristics that permits the support structures to react more strongly to the acoustic standing wave than other materials in the fluid mixture.

The support structures may be agitated in the column to enhance the affinity process. In different modes, the column fluid mixture that passes through the acoustic standing wave can be recirculated to the column or not. The fluid flow in the column can be controlled to flow or not, and when flowing, the rate of flow can be controlled. The fluid may be stationary in the column and may have other processes applied thereto, such as temperature adjustment, agitation, incubation, and/or any other useful process. The volume of the column can be effectively modified, such as with the provision of a plunger or piston in the column. Heating or cooling can be applied to the column or the contents of the column, internally or externally to the column.

The particulates may include beads, and wherein at least one of the beads comprises a sphere with a diameter of about 20 to 300 µm and comprises at least one of DEAE (N, N-diethylaminoethyl)-dextran, glass, polystyrene plastic, acrylamide, collagen, or alginate. The cell-supporting material may include microbubbles that have a surface coating for growth of the cells. The cells may include, for example, T-cells, MRC-5 cells or stem cells.

An acoustic transducer can be used to generate the acoustic standing wave, which can generate pressure forces in one or multiple dimensions. In multiple dimensions, the acoustic standing wave forces can be of the same order of magnitude. For example, forces in the direction of wave propagation may be of the same order of magnitude as forces that are generated in a different direction. An interface region can be generated near a border of the acoustic standing wave that contributes to preventing support structures from passing. Multiple transducers may be used, some for generating an acoustic wave in one or modes, and others for generating an acoustic wave in another, different mode. For example, the acoustic wave can be a standing wave that can generate pressure forces in one dimension or in multiple dimensions. The acoustic wave can be generated in a mode to form an interface region to prevent passage of certain materials while permitting passage of other materials. The acoustic wave can be generated in a mode to trap and cluster certain materials that build in size until the gravity or buoyancy forces on the clusters surpass the other forces on the clusters, such as fluidic or acoustic forces, so that the clusters drop or rise out of the acoustic wave.

Collecting cells may be performed with or without turning off the acoustic transducer. An additive which enhances aggregation of the support structures into the flow chamber may be applied. The method may further include recirculating the support structures, such as beads, to a culturing chamber coupled to the flow chamber. The method may also include processing the collected cells for infusion into a subject patient. Subsequent to preferentially trapping, the method may include allowing the trapped cells and/or cell-supporting material to rise or settle out of the fluid due to a buoyance or gravity force. The rising or settling cells and/or support material may exit the flow chamber. The mode of trapping cells or support material for separation by rising or settling out of the fluid may be accompanied by a mode of preventing or permitting the cells and/or support material from passing through a fluid path. The mode of preventing or permitting passage may be implemented with an acoustic wave with an interface region across the fluid path.

In some example implementations, the material includes target compounds, such as recombinant proteins and monoclonal antibodies, viruses, and/or live cells (e.g., T cells). Beads or microcarriers with or without functionalized material on their surfaces may be the target compounds or components.

An example apparatus may include a flow chamber configured to receive fluid containing functionalized material. The flow chamber may be in the form of a column. An acoustic transducer is arranged in relation to the flow chamber, for example, acoustically coupled to the flow chamber, to provide an acoustic wave or signal into the flow chamber when excited. Excitation of the transducer can generate a multi-dimensional acoustic field inside the chamber that includes first spatial locales where acoustic pressure amplitude is elevated from a base level, such as, for example when the acoustic transducer is turned off, and second spatial locales where acoustic pressure amplitude has little or no elevation from the base level, for example the acoustic pressure amplitude may be equivalent to that when the acoustic transducer is turned off.

In some modes, the functional material may be driven to and retained at the first or second locales of the multidimensional acoustic field. In other modes, the functional material may be prevented from entering the multidimensional acoustic field in accordance with an edge effect at an interface region. Materials to be processed that include target materials for separation may be flowed into the flow chamber where functionalized material is retained such that a portion of the target materials with features complementary to the functionalized material become bound to the functionalized material while other portions of the materials pass through the flow chamber. The chamber may be configured for vertical flow which may be in an upward or downward direction. Fluid paths to the chamber may be provided at a top and/or bottom of the chamber. An acoustic transducer can be coupled to a top and/or bottom of the chamber to generate an acoustic field at that locale.

The functionalized microcarriers may also be circulated after the recombinant proteins or monoclonal antibody is eluted from the surface by a buffer or other process elution. This allows for greater surface area and affinity interaction of the functionalized microcarriers with the expressed proteins from the bioreactor, increasing the efficiency of the acoustic fluidized bed chromatography process.

In some example implementations, the apparatus provides functionalized particles, such as beads, in an arrangement that provides more space between particles, such as beads or cells, than packed columns. The lower density decreases the likelihood that non-target biomaterials will clog flow paths between the functionalized particles. In some example implementations, recirculating media containing the target biomaterials in effect increases the capture surface area of the apparatus by passing free target biomaterials past the functionalized particles multiple times. The reduced contact of non-target biomaterials such as cells can help preserve the viability of cells. The technology described here can be used in high- or low-density cell culture, new research applications, large production culture volumes, e.g., more than 1,000 liters, efficient monitoring and culture control, reduction of costs and contamination in cell culture applications.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE SEVERAL VIEWS OF THE DRAWINGS

The disclosure is described in greater detail below, with reference to the accompanying drawings, in which.

DETAILED DESCRIPTION

This disclosure describes methods, systems and apparatuses that employ an acoustic standing wave with nodes and antinodes to separate support structures such as beads or coated microbubbles from other materials in a chamber such as a column. The example implementations described herein may be operated in different modes. For example, in some modes, an acoustic wave is generated with certain characteristics across the chamber. The acoustic wave may be generated by an acoustic transducer, which may be located at one end of the column. The acoustic wave may cause an interface region to be generated that blocks certain materials from entering the acoustic wave, while permitting passage of other materials. The acoustic wave characteristics can be controlled to block or pass materials based on parameters such as compressibility, density, size, acoustic contrast factor, and any other parameter that is responsive to the acoustic waves. In other modes, an acoustic wave is generated with spatial locales that capture materials to form clusters that increase in size to a point where the gravity or buoyancy force on the cluster exceeds that of the acoustic or fluid drag force, causing the cluster to exit the acoustic wave.

The modes discussed herein may be employed together or separately or in combination. The modes may be employed or generated with one or more acoustic transducers. The acoustic field generated by the acoustic wave can be configured to block or permit passage of certain materials. For example, support structures for cells, which may be in the form of beads, bead/cell complexes or particles, may be blocked from passage through the acoustic field. Materials such as cells may be passed through the fluid chamber. The support structures include functionalized material that can bind with at least some of the material passed through the fluid chamber. The material that is bound to the support structures via the functionalized material is retained in the fluid chamber by the support structures being retained in the fluid chamber with the acoustic wave. Material that is not bound to the support structures may pass out of the fluid chamber through the acoustic wave. The technique of using acoustic waves to perform affinity separation obtains a number of advantages as described in more detail herein.

Figure 1:
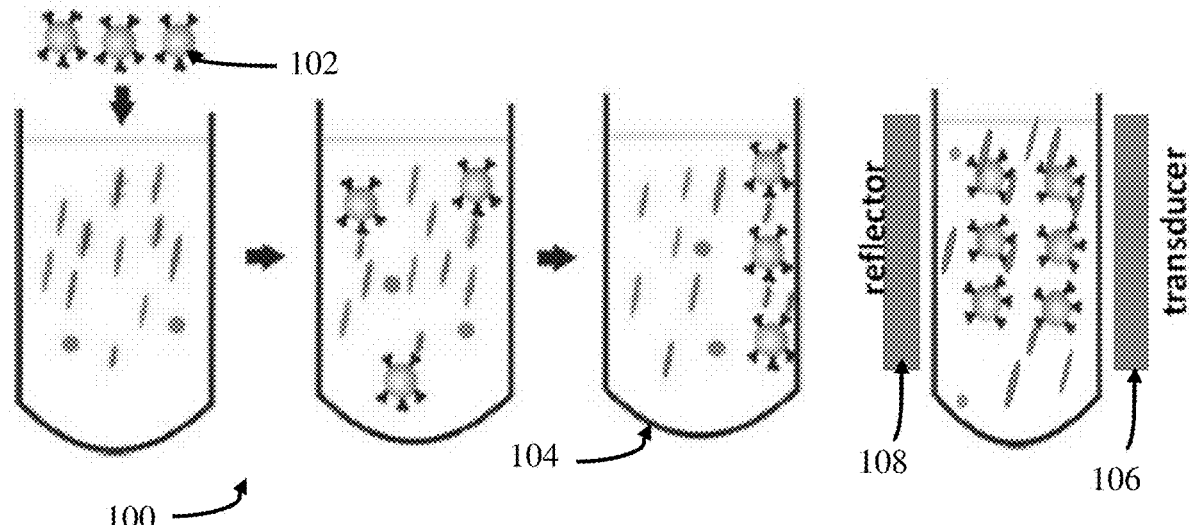
FIG. 1 is a simplified diagram of an acoustic affinity process.

Referring to FIG. 1, a diagram illustrates an acoustic affinity process 100. Functionalized beads 102 are placed in a chamber 104 that contains targeted and non-targeted material. The target material corresponds to the functionalization provided to beads 102. Process 100 illustrates the target material being bound to beads 102 in an affinity binding process. Beads 102 are collected or influenced by an acoustic standing wave generated by transducer 106 between transducer 106 and reflector 108. The remaining material in chamber 104 can be removed by flowing fluid through chamber 104 while beads 102 are retained by the acoustic wave. Process 100 illustrated in FIG. 1 can be a positive or negative selection process, where the target material is desired to be itself collected or removed from the other materials, respectively.

In accordance with some examples, an acoustic affinity system is implemented that can include the features of being closed, automated and/or single-use. The system can be considered closed if the components can be sealed from an open-air environment. An automated system is able to operate autonomously, with little or no operator intervention. The system is single use when components and materials employed for an affinity separation run, which may include multiple recirculations, are disconnected and discarded after an affinity separation run. A single use system can avoid the additional steps of cleaning and sterilizing the equipment components and materials for subsequent runs.

Previous systems for affinity separation employed magnetically responsive beads. These beads may incur challenges during manufacturing processes as they do not dissolve or are not readily consumed in vivo and are preferentially completely removed from any treatment supplied to a patient. While such beads may be used in the present acoustic affinity separation system, the use of acoustics offers the possibility for the use of support structures, such as beads, that are tailored to be specifically acoustically responsive. For example, the beads can be nonmagnetic or non-magnetically responsive, and highly acoustically responsive. The acoustically responsive beads can be composed of a variety of materials, significantly increasing the flexibility of the processing system in which they are employed. These acoustic affinity beads can be composed of dissolvable material that is biocompatible, which can alleviate aggressive bead removal processes that are employed with magnetically responsive beads.

The acoustic affinity system can be configured to have increased throughput compared with current systems. For example, the fluid flow rate through the system can be increased over that typically used with conventional affinity systems. The system can be configured with larger channels that permit higher flow rates and volumes. The expansion of the cell population can be implemented within the presently disclosed systems or can be implemented externally and fed to the acoustic affinity system.

The configuration of the acoustic affinity system permits the use of multiple types of support structures or beads that may have different characteristics, such as different ranges of sizes or densities. The different groups of support structures or beads may be provided with different types of functionalized material such as proteins, antigens or antibodies to thereby enable multiplexing of affinity separation. This configuration permits complex, single-pass affinity selections to be realized.

In some example implementations, a column is provided with a volume of beads that have an affinity for a certain type of cell. Cells introduced into the column form a complex with the beads, which complexes can be separated from the column volume using acoustic techniques. The separation may be leveraged to harvest cultured cells of interest, and the extracted cells may be infused into a patient. Using acoustics with an affinity binding system to separate cultured cells of interest can be applicable to a variety of cell therapy applications, e.g., vaccine therapies, stem cell therapies, particularly allogenic and autologous therapies, or regenerative therapies.

An acoustic wave is generated in a flow chamber, such as a column, to effectuate separation of beads and bead complexes from unbound cells or materials in a fluid. The separation can be negative or positive, where the unwanted material to be excluded is bound to the beads, or where the material desired in the separation is bound to the beads, respectively. The material of interest, for either negative or positive selection, may be different types of cells, including adherent cells. Example adherent cells may include human multipotent stem cells (hMSC), human mesenchymal stem cells (also hMSC), human pluripotent stem cells (hPSC), human dermal fibroblasts (hDF), human chondrocytes, and some T lymphocytes. Adherent cells may differ in their antigen specificity (e.g. CD8 adherent cell). The lines used in cell therapy may be mono- or polyclonal (e.g. polyclonal CD8 adherent cell line), and CAR (chimeric antigen receptor) adherent cells (a.k.a. artificial adherent cell receptors, or chimeric adherent cell receptors, or chimeric immunoreceptors. These are T-cells modified to recognize a specific protein. The beads employed in the acoustic affinity separation system can be configured to bind or not bind to these cells or material of interest for negative or positive selection.

The bead technology described here can be used in high density cell culture, new research applications, large production culture volumes, e.g., more than 1,000 liters, efficient monitoring and culture control, reduction of costs and contamination in cell culture applications. The beads used may be commercially available, such as the MAGNE magnetic affinity beads or polystyrene beads supplied by Promega Corporation or MACS beads supplied by Miltenyi Biotec. The size of the beads, for example their diameter, may be in the nanometer or micrometer range. Cospheric beads may be used, which are beads with at least two layers. The layers may have different characteristics, such as differing contrast factors, structural rigidity, or any other characteristics that are desired to be combined in a single bead through the use of multiple layers.

Some implementations may use microbubbles as support structures to bind material of interest. The microbubbles can be composed by a shell of biocompatible materials and ligands capable of linking to the cells or material of interest, including proteins, lipids, or biopolymers, and by a filling gas. Low density fluids may be used for relative ease of manufacturing. The microbubble shell may be stiff (e.g., denaturated albumin) or flexible (phospholipids) and presents a thickness from 10 to 200 nm. The filling gas can be a high molecular weight and low-solubility filling gas or liquid (perfluorocarbon or sulfur hexafluoride), which can produce an elevated vapor concentration inside the microbubble relative to the surrounding fluid, such as blood, and increase the microbubble stability in the peripheral circulation. The microbubble shell can have a surface coating such as a lipid layer. The lipid layer may be utilized as scaffolds or substrates for material growth such as cells or biomolecules. Active groups may be easier to conjugate directly to the glass surface. The microbubbles may have a diameter in a range of 2 to 6 micrometers. The coated microbubbles may have a negative contrast factor.

Examples discussed above provide beads as support structures. Other support structures such as coated bubbles or microbubbles can be also used. For the sake of convenience, support structures may be referred to herein collectively as beads, which term is intended to encompass all types of support structures, including beads, bubbles, microcarriers and any other type of affinity material/support structure that can bind to or be bound to a target material of interest.

Cells are bound to beads, e.g., CD3/CD28 activated beads. As discussed in further detail below, the beads can be functionalized with surface chemistry such that the cells or material of interest can be attached to or adherent to the surface of the beads. The beads can include support matrices allowing for the growth of adherent cells in bioreactors or other cell culturing systems. In some cases, adherent cells will bind to the beads without the antigens on the surface and the beads can be functionalized or non-functionalized. Some examples of affinity applications include positive or negative selection of CD3+, CD3+CD4+ and/or CD3+CD8+ affinity selection for apheresis products. Other examples of affinity applications include positive or negative selection of TCR+ or TCR− cells.

Structurally, the beads include spheres with a diameter in a range of 1 to 300 µm, e.g., in the range of 125 to 250 µm. The spheres can have densities in a range of 1.02-1.10 g/cm$^3$. In some instances, the beads can also include rod-like structures. The beads may be smooth or macroporous.

The core of the beads can be made from different materials, such as glass, polystyrene plastic, acrylamide, collagen, and alginate. The bead materials, along with different surface chemistries, can influence cellular behavior, including morphology and proliferation.

The beads can be coated with a variety of coatings such as glass, collagen (e.g., neutral or charged gelatin), recombinant proteins or chemical treatments to enhance cell attachment, which may lead to more desirable cell yields for a number of different cell lines.

Surface chemistries for the beads can include extracellular matrix proteins, recombinant proteins, peptides, and positively or negatively charged molecules. The surface charges of the micro carriers may be introduced from a number of different groups, including DEAE (N,N-diethylaminoethyl)-dextran, laminin or vitronectin coating (extra cellular matrix proteins). In the DEAE-dextran example, a mild positive charge can be added to the surface.

Other examples of bead coatings, for example with functionalized material for use in biological affinity processes, include streptavidin, monomeric avidin, protein A, anti-CD3, as well as other known functionalized material for binding biological material. Various combinations of antibodies, reagents and/or functionalized material can be used with the beads to bind to a cell of interest. A cell of interest may be identified with target proteins or markers, such as CD3, for example.

In some implementations, the beads are formed by substituting a cross-linked dextran matrix with positively charged DEAE groups distributed throughout the matrix. This type of bead can be used for established cell lines and for production of viruses or cell products from cultures of primary cells and normal diploid cell strains.

In some implementations, the beads are formed by chemically coupling a thin layer of denatured collagen to the cross-linked dextran matrix. Since the collagen surface layer can be digested by a variety of proteolytic enzymes, it provides opportunities for harvesting cells from the beads while maintaining increased or maximum cell viability and membrane integrity. The acoustic affinity system discussed herein can be operated with a number of types of beads, three general groupings of which are discussed below.

The beads may be constructed and configured according to cGMP (current good manufacturing practice) standards or regulations. One example group of beads that may be used in the acoustic affinity system are large, dense beads. These large beads may possess the following characteristics.

Non-magnetic
Average size of about 50 um
Slower binding kinetics
More easily separated using acoustic techniques
Positive acoustic contrast factor
Dissolvable and biocompatible
poly(lactic-co-glycolic acid), PLGA
Not internalized by cells Another example group of beads are those referred to herein as medium sized beads. These medium sized beads may possess the following characteristics.

Non-magnetic
Average size in the range of about 1-10 um
Dissolvable and biocompatible
Binding kinetics faster than large beads Use large acoustic contrast
Negative and positive contrast
PLGA or proprietary lipid-based Another example group of beads are those referred to herein as small beads. These small beads may possess the following characteristics.

Non-magnetic
Average size in the range of about 200 nm-2 um
Dissolvable and biocompatible
Very fast binding
Separation through clustering
Negative contrast factor, low speed of sound & high density
Proprietary lipid-based Different types of beads may be chosen for different types of applications. For example, larger beads may be used when the cells are cultured with the beads, or when the affinity binding takes place in a non-flowing mode.

The beads used for the affinity binding can be held back by or passed through an acoustic wave generated by an acoustic transducer. The acoustic transducer may generate a multi-dimensional acoustic standing wave in a flow chamber to create an acoustic field that includes locales of increased pressure radiation forces. The acoustic transducer can include a piezoelectric material that is excited to vibrate and generate an acoustic wave. The acoustic transducer can be configured to generate higher order vibration modes. For example, the vibrating material in the acoustic transducer can be excited to obtain a standing wave on the surface of the vibrating material. The frequency of vibration is directly related to the frequency of the excitation signal. In some implementations, the vibrating material is configured to have an outer surface directly exposed to a fluid layer, e.g., the fluid or mixture of beads and cultured cells in a fluid flowing through the flow chamber. In some implementations, the acoustic transducer includes a wear surface material covering an outer surface of the vibrating material, the wear surface material having a thickness of a half wavelength or less and/or being a urethane, epoxy, or silicone coating, polymer, or similar thin coating. In some implementations, the acoustic transducer includes a housing having a top end, a bottom end, and an interior volume. The vibrating material can be positioned at the bottom end of the housing and within the interior volume and has an interior surface facing to the top end of the housing. In some examples, the interior surface of the acoustic material is directly exposed to the top end housing. In some examples, the acoustic transducer includes a backing layer contacting the interior surface of the acoustic material, the backing layer being made of a substantially acoustically transparent material. One or more of the configurations can be combined in the acoustic transducer to be used for generation of a multi-dimensional acoustic standing wave.

The generated multi-dimensional acoustic standing wave can be characterized by strong gradients in the acoustic field in all directions, not only in the axial direction of the standing waves but also in lateral directions. In some instances, the strengths of such gradients are such that the acoustic radiation force is sufficient to overcome drag forces at linear velocities on the order of mm/s. Particularly, an acoustic radiation force can have an axial force component and a lateral force component that are of the same order of magnitude. As a consequence, the acoustic gradients result in strong trapping forces in the lateral direction.

The multi-dimensional acoustic standing wave can give rise to a spatial pattern of acoustic radiation force. The multidimensional acoustic standing wave may be generated from one transducer and reflector pair due to the multimode perturbations of the piezoelectric material in the transducer. The acoustic radiation force can have an axial force component and a lateral force component that are of the same order of magnitude. The spatial pattern may manifest as periodic variations of radiation force. More specifically, pressure node planes and pressure anti-node planes can be created in a fluid medium that respectively correspond to floor acoustic radiation force planes with maximum and minimum acoustic radiation force planes in between pressure nodal and anti-nodal planes. Pressure nodal planes are also acoustic displacement anti-nodal planes, and vice versa. The spatial pattern may function much like a comb filter in the fluid medium.

In some modes, discussed in greater detail below, the spatial pattern may create an interface region that blocks entry of particles with certain characteristics from entering or crossing the acoustic wave. In other modes of operation, discussed in greater detail below, the spatial pattern may be used to trap particles, for example, of a particular size or size range, while particles of a different size or size range may not be trapped. The modes may be employed separately or together in combination to provide both a barrier and trapping function, in the same or separate locale.

In a multidimensional acoustic standing wave, the acoustic radiation forces within a particular pressure nodal plane are such that particles are trapped at several distinct points within these planes. The trapping of particles leads to the formation of cluster of particles, which continuously grow in size, and, upon reaching a critical size, settle out or rise out of the primary fluid continuously because of enhanced gravitation or buoyancy settling. For example, the spatial pattern can be configured, for example, by adjusting the insonification frequency and/or phase, power, voltage and/or current supplied to the transducer, or fluid velocity or flow rate, to allow the cultured cells to freely flow through while trapping the support structures, such as beads or microbubbles, thereby separating at least the trapped support structures from cells or other materials in the fluid.

In some example implementations, one or more multi-dimensional acoustic standing waves are generated between an ultrasonic transducer and a reflector. An acoustic wave is continually launched from the acoustic transducer and reflected by the reflector to interfere with the launched acoustic wave to form an acoustic standing wave. The formation of the acoustic standing wave may depend on a number of factors, including frequency, power, medium, distance between the transducer and reflector, to name a few. The standing wave can be offset at the transducer or the reflector so that local minima or maxima are spaced from the transducer or from the reflector. The reflected wave (or wave generated by an opposing transducer) can be in or out of phase with the transducer generated wave. The characteristics of the standing wave can be modified and/or controlled by the drive signal applied to the transducer, such as by modifying and/or controlling the phase, amplitude or frequency of the drive signal. Acoustically transparent or responsive materials may also be used with the transducer or reflector to modify and/or control the standing wave.

As the fluid mixture flows between an ultrasonic transducer and reflector, or two facing ultrasonic transducers, between which one or more multi-dimensional acoustic standing waves are established, particles or secondary fluid cluster, collect, agglomerate, aggregate, clump, or coalesce. The clustering of material may take place at the nodes or anti-nodes of the multi-dimensional acoustic standing wave, depending on the particles' or secondary fluid's acoustic contrast factor relative to the host fluid. The particles form clusters that eventually exit the multi-dimensional acoustic standing wave nodes or anti-nodes when the clusters have grown to a size large enough to overcome the holding force of the multi-dimensional acoustic standing wave. For example, the clusters grow in size to a point where the gravity or buoyancy forces become dominant over the acoustic or fluid drag forces, causing the clusters to respectively sink or rise. For fluids/particles that are denser than the host fluid, such as is the case with most cells, the clusters sink and can be collected separately from the clarified host fluid. For fluids/particles that are less dense than the host fluid, the buoyant clusters float upwards and can be collected.

The scattering of the acoustic field off the particles creates secondary acoustic forces that contribute to driving particles or fluid droplets together. The multi-dimensional acoustic standing wave generates a three-dimensional acoustic radiation force, which acts as a three-dimensional trapping field. The acoustic radiation force is proportional to the particle volume (e.g. the cube of the radius) when the particle is small relative to the wavelength. The force is proportional to frequency and the acoustic contrast factor. The force scales with acoustic energy (e.g. the square of the acoustic pressure amplitude). When the acoustic radiation force exerted on the particles is stronger than the combined effect of fluid drag force and buoyancy and gravitational force, the particles are trapped within the acoustic standing wave. The particle trapping in a multi-dimensional acoustic standing wave results in clustering, concentration, agglomeration and/or coalescence of the trapped particles. Relatively large solids of one material can thus be separated from smaller particles of a different material, the same material, and/or the host fluid through enhanced gravitational/buoyancy separation.

The multi-dimensional standing wave generates acoustic radiation forces in a number of directions, including in the direction of acoustic wave propagation and in a direction that is the lateral to the acoustic wave propagation direction. As the mixture flows through the acoustic chamber, particles in suspension experience a strong axial force component in the direction of the standing wave. Since this acoustic force is across (e.g. perpendicular to) the flow direction, it is not aligned with the fluid drag force. The acoustic force can thus quickly move the particles to pressure nodal planes or anti-nodal planes, depending on the contrast factor of the particle. The lateral acoustic radiation force acts to move the concentrated particles towards the center of each planar node, resulting in clustering, agglomeration or clumping. The lateral acoustic radiation force component can overcome fluid drag for such clumps of particles, to continually grow the clusters, which can exit the mixture due to dominant gravity or buoyancy forces. The drop in drag per particle as the particle cluster increases in size, as well as the drop in acoustic radiation force per particle as the particle cluster grows in size, may separately or collectively influence operation of the acoustic separator device. In the present disclosure, the lateral force component and the axial force component of the multi-dimensional acoustic standing wave are of the same or different order of magnitude. In a multi-dimensional acoustic standing wave generated by a single transducer, the axial force can be comparable with the lateral force. The lateral force of such a multi-dimensional acoustic standing wave is much higher than the lateral force of a planar standing wave, usually by two orders of magnitude or more.

The multi-dimensional acoustic standing wave generated for various modes, including to form a barrier or for clustering, is obtained by exciting a piezoelectric material at a frequency that excites a fundamental 3D vibration mode of the transducer. The transducer may be composed of various materials that may be perturbed to generate an ultrasonic wave. For example, the transducer may be composed of a piezoelectric material, including a piezoelectric crystal or poly-crystal. Perturbation of the piezoelectric material, which may be a piezoelectric crystal or poly-crystal, in the ultrasonic transducer to achieve a multimode response allows for generation of a multidimensional acoustic standing wave. A piezoelectric material can be specifically designed to deform in a multimode response at designed frequencies, allowing for generation of a multi-dimensional acoustic standing wave. The multi-dimensional acoustic standing wave may be generated with distinct modes of the piezoelectric material such as a 3×3 mode that generates nine separate multidimensional acoustic standing waves. A multitude of multidimensional acoustic standing waves may also be generated by allowing the piezoelectric material to vibrate through many different mode shapes. Thus, the material can be selectively excited to operate in multiple modes such as a 0×0 mode (i.e. a piston mode), 1×1, 2×2, 1×3, 3×1, 3×3, and other higher order modes. The material can be operated to cycle through various modes, in a sequence or skipping past one or more modes, and not necessarily in a same order with each cycle. This switching or dithering of the material between modes allows for various multidimensional wave shapes, along with a single piston mode shape to be generated over a designated time. The transducers may be composed of a piezoelectric material, such as a piezoelectric crystal or poly-crystal, which may be made of PZT-8 (lead zirconate titanate). Such crystals may have a major dimension on the order of 1 inch and larger. The resonance frequency of the piezoelectric material may nominally be about 2 MHz and may be operated at one or more frequencies. Each ultrasonic transducer module may include single or multiple crystals. Multiple crystals can each act as a separate ultrasonic transducer and are can be controlled by one or multiple controllers, which controllers may include signal amplifiers. The control of the transducer can be provided by a computer control that can be programmed to provide control signals to a driver for the transducer. The control signals provided by the computer control can control driver parameters such as frequency, power, voltage, current, phase, or any other type of parameter used to excite the piezoelectric material. The piezoelectric material can be square, rectangular, irregular polygon, or generally of any arbitrary shape. The transducer(s) is/are used to create a pressure field that generates forces of the same order of magnitude in a lateral and an axial direction.

In some examples, the size, shape, and thickness of the piezoelectric material can determine the transducer displacement at different frequencies of excitation. Transducer displacement with different frequencies can be used to target certain material in an ensonified fluid. For example, higher frequencies with shorter wavelengths can target smaller sized material. Lower frequencies with longer wavelengths can target smaller sized material. In these cases of higher and lower frequencies, material that is not influenced by the acoustic wave may pass through without significant change. Higher order modal displacements can generate three-dimensional acoustic standing waves with strong gradients in the acoustic field in all directions, thereby creating strong acoustic radiation forces in all directions, which forces may, for example be equal in magnitude, leading to multiple trapping lines, where the number of trapping lines correlate with the particular mode shape of the transducer.

The piezoelectric crystals of the transducers described herein can be operated at various modes of response by changing the drive parameters, including frequency, for exciting the crystal. Each operation point has a theoretically infinite number of vibration modes superimposed, where one or more modes are dominant. In practice, multiple vibration modes are present at arbitrary operating points of the transducer, with some modes dominating at a given operating point.

Figure 2:
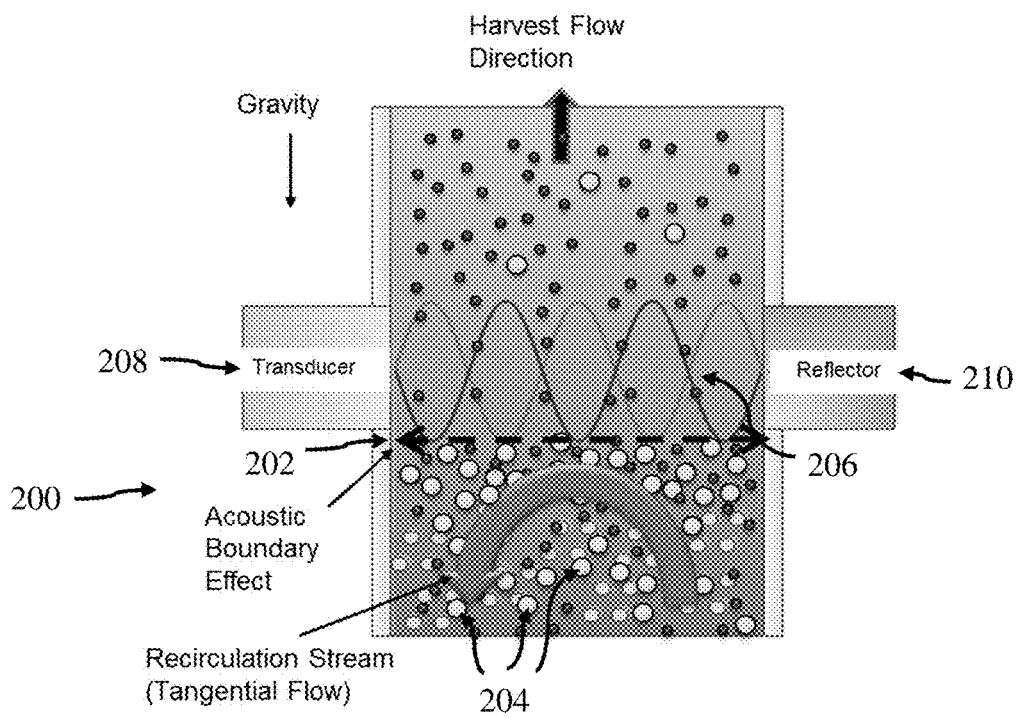
FIG. 2 is a side elevation view of an acoustic affinity system operated in an edge effect mode.

Referring to FIG. 2, a system 200 operating in interface barrier mode is illustrated. An acoustic interface region 202 is employed to block beads 204 from passing through acoustic wave 206. Acoustic wave 206 is generated by an acoustic transducer 208 continually launching an acoustic wave that is reflected by a reflector 210 to generate a standing wave with localized minima (nodes) and maxima (anti-nodes). A pressure rise may be generated on the upstream side of acoustic wave 206 at interface region 202, along with an acoustic radiation force acting on the incoming suspended particles. Interface region 202, also referred to as providing an edge, boundary or barrier effect, can act as a barrier to certain materials or particles. In system 200, a majority, or substantially all, of beads 204 are prevented from entering acoustic wave 206. Other materials can pass through interface region 202. Acoustic wave 206 is configured to influence beads 204, while other material experiences a lower influence to permit them to pass through acoustic wave 206.

Interface region 202 is located at an upstream bounding surface or region of the volume of fluid that is ensonified by acoustic transducer 208. For example, the fluid may flow across interface region 202 to enter the ensonified volume of fluid and continue in a downstream direction. The frequency of acoustic standing wave 206 may be controlled to have desired characteristics, such that, for example, different contrast factor materials may be held back by or allowed through acoustic standing wave 206. Interface region 202 can be generated and controlled to influence, for example, particles of a first size range to be retained. Acoustic standing wave 206 can be generated and controlled to permit, for example, particles of a second size range that is different from the first to pass through. Acoustic standing wave 206 that forms interface region 202 may be modulated so as to block or pass selective materials. The modulation can be employed to block or pass selective materials at different times while fluid flows through the acoustic field generated by acoustic standing wave 206.

In some example implementations, acoustic standing wave 206 produces a three-dimensional acoustic field, which, in the case of excitation by transducer 208 implemented as a rectangular transducer, can be described as occupying a roughly rectangular prism volume of fluid across the direction of fluid flow. Acoustic wave 206 can be generated as a standing wave. The generation of acoustic wave 206 can be achieved with two transducers facing each other across the fluid flow. A single transducer, e.g., transducer 208, may be used to launch acoustic wave 206 through the fluid toward an interface boundary region that provides a change in acoustic properties, such as may be implemented with a chamber wall or reflector 210. The acoustic wave reflected from the interface boundary can contribute to forming a standing acoustic wave with the acoustic wave launched from transducer 208. During operation at different or changing flow rates, the location of interface region 202 may move upstream or downstream.

The acoustic field generated by acoustic standing wave 206 exerts an acoustic radiation pressure (e.g., a pressure rise) and an acoustic radiation force on the fluid and materials at interface region 202. The radiation pressure influences material in the fluid to block upstream materials with certain characteristics from entering the acoustic field. Other materials with different characteristics than the blocked materials are permitted to pass through the acoustic field with the fluid flow. The characteristics that affect whether the materials or particles are blocked or passed by the acoustic field include material compressibility, density, size and acoustic contrast factor. The parameters that can influence the generation or modulation of the acoustic wave include frequency, power, current, voltage, phase or any other drive parameters for operating transducer 208. Other parameters impacting acoustic wave 206 include transducer size, shape, thickness, as well as chamber size and fluid parameters such as density, viscosity and flow rate.

Figure 3:
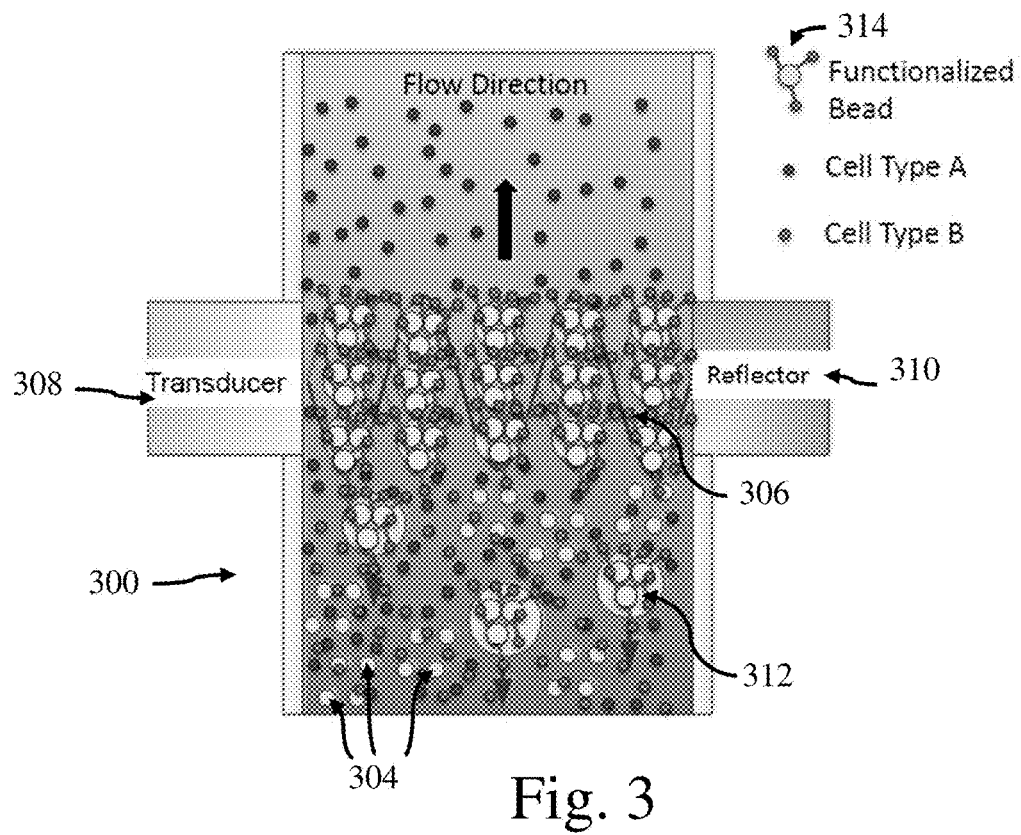
FIG. 3 is a side elevation view of an acoustic affinity system operated in a cluster mode.

Referring to FIG. 3, a system 300 operating in clustering mode is illustrated. One or more multi-dimensional acoustic standing waves 306 are created between an ultrasonic transducer 308 and a reflector 310. An acoustic wave is continually launched from acoustic transducer 308 and reflected by reflector 310 to interfere with the launched wave, thereby forming a standing wave 306 that has local minima and maxima, or nodes and anti-nodes, respectively. The reflected wave (or wave generated by an opposing transducer) can be in or out of phase with the transducer-generated wave. The characteristics of the standing wave can be modified and/or controlled by the drive signal applied to transducer 308, such as by modifying and/or controlling the phase, amplitude or frequency of the drive signal. Acoustically transparent or responsive materials may also be used with transducer 308 or reflector 310 to modify and/or control standing wave 306.

In a clustering mode, beads 304, bead complexes 314 and/or particles such as cells cluster, collect, agglomerate, aggregate, clump, or coalesce within multi-dimensional standing wave 306. The clustering may occur at the nodes or anti-nodes of multi-dimensional acoustic standing wave 306, depending on the acoustic contrast factor of beads 304 or the particles relative to the host fluid. For example, beads 304, bead complexes 314 or particles that have a positive acoustic contrast factor are driven to the nodes of multi-dimensional acoustic standing wave 306, while beads 304, bead complexes 314 or particles that have a negative acoustic contrast factor are driven to the anti-nodes. The clustered beads 304, bead complexes 314 or particles form clusters 312 that eventually exit the nodes or anti-nodes of multi-dimensional acoustic standing wave 306 when clusters 312 have grown to a size large enough to overcome the holding force of multi-dimensional acoustic standing wave 306. For example, as clusters 312 grow in size in multi-dimensional acoustic standing wave 306, gravity or buoyancy forces begin to dominate over acoustic and/or fluid drag forces. Once the size of a cluster 312 is large enough to cause the gravity or buoyancy forces on cluster 312 to exceed the acoustic and/or fluid drag forces, cluster 312 exits multi-dimensional acoustic standing wave 306.

For beads 304, bead complexes 314 or particles that, for example, have a positive acoustic contrast factor, clusters 312 typically sink with gravity forces. For beads 304, bead complexes 314 or particles that, for example, have a negative acoustic contrast factor, clusters 312 typically rise with buoyancy forces. Gravity is not depicted in FIG. 3, and the orientation of system 300 can be with gravity aligned with or against the fluid flow direction. With gravity against the direction of fluid flow, clusters 312 are depicted as sinking due to gravity forces. With gravity aligned with the direction of fluid flow, clusters 312 are depicted as rising due to buoyancy forces.

In this mode of operation, beads 304, and bead complexes 314, are retained in the chamber by sinking or rising out of the acoustic wave. The beads tend to be lightly clustered in this mode and tend to be redistributed in the chamber to permit additional interaction with target material or cells. In addition, an agitator can be provided to the chamber to promote movement and redistribution of the clustered beads.

Particles such as cell Type A are not captured in multi-dimensional acoustic standing wave 306. The characteristics of the Type A cells and multi-dimensional acoustic standing wave 306 permit the Type A cells to pass without being captured and/or clustering. The Type B cells are bound to beads 304 to form bead complexes 314. Accordingly, Type B cells may themselves pass through multi-dimensional acoustic standing wave 306 but may be driven into a cluster 312 if bound to beads 304.

Figure 4:
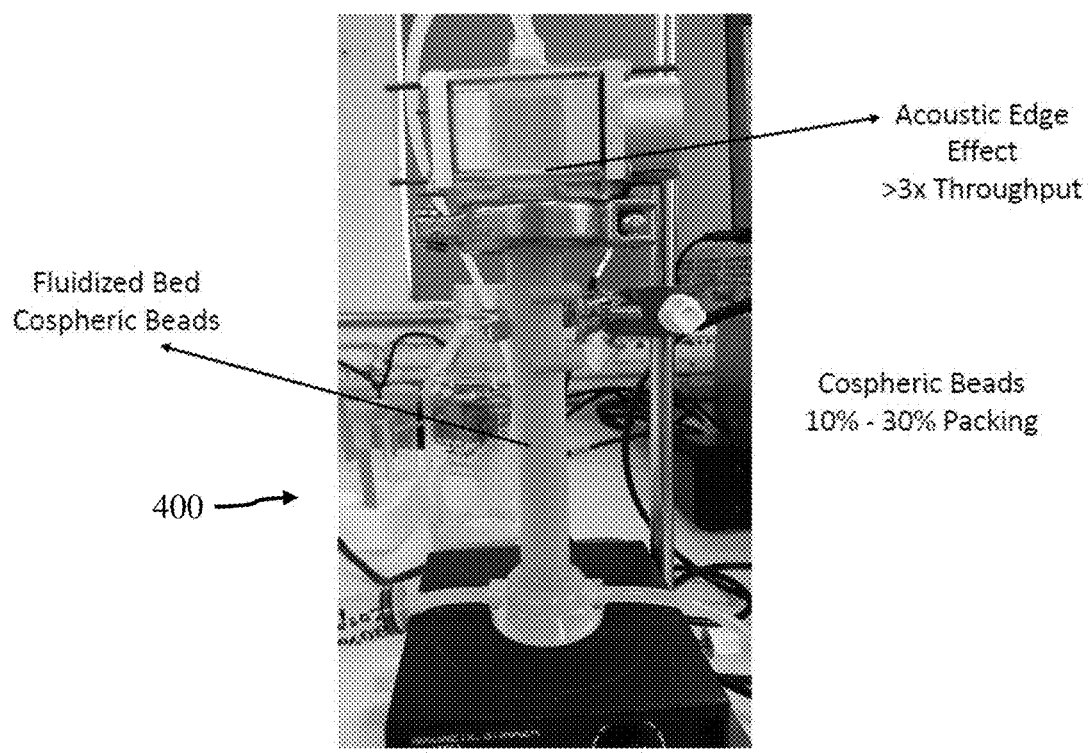
FIG. 4 is a photograph of a front elevation view of a fluidized bed set up.

Referring to FIG. 4, a set up for a fluidized bed system 400 is illustrated. The fluidized bed is composed of cospheric beads with a range of about 10% to about 30% packing. The acoustic transducer is attached to a top of the column housing the fluidized bed. Connections are provided at a base of the column for introducing or removing fluid that may entrain beads, cells or other materials. The configuration and operation of system 400 can be controlled with a controller that provide signals to operate a driver for the transducer, as well as fluid control devices, such as pumps, valves or switches. The controller receives feedback from sensors, which can include turbidity sensors, fluid flow sensors and/or valve sensors. The controller also receives feedback from the acoustic transducer to contribute to providing a close loop transducer control. The different modes of operation of the transducer(s) can be implemented by the controller. The controller can be employed to provide automated operation for system 400 in accordance with the examples discussed herein. For example, the controller can be provided with a number of automation profiles from which an operator can select to implement an automated acoustic affinity cell selection process. As illustrated in FIG. 4, the acoustic transducer is employed in a mode to generate an edge effect or interface region as discussed above. Testing on the throughput of the column with the transducer operated in this mode has established some guidelines for flow velocities or flow rates that can be employed in the column while the beads are maintained in the column by the acoustic standing wave and edge effect.

Figure 5:
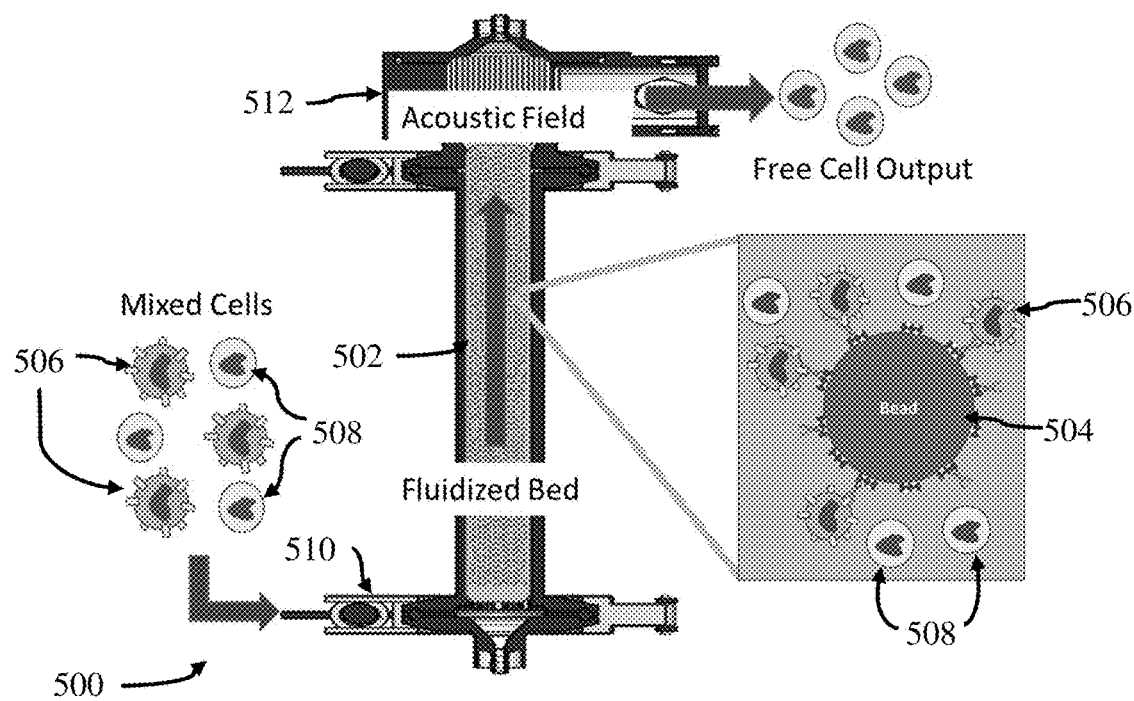
FIG. 5 is a diagram of an acoustic affinity system and process.

Referring to FIG. 5, a fluidized bed system 500 is illustrated. In this example implementation, column 502 is packed with affinity beads 504, which may be in the range of about 10% to about 30% packing where % packing indicates the percentage of bead volume versus volume of the entire column. Beads 504 are provided with affinity structures to bind to target cells 506. An acoustic transducer 512 capable of generating an acoustic field is coupled to a top of column 502. In operation, a mix of target cells 506 and nontargeted cells 508 is input into column 502 via an inlet 510. As the mix of cells flows through column 502, target cells 506 bind with beads 504. Nontargeted cells 508 tend not to bind with beads 504 for lack of a complementary affinity structure. As the mixture flows through column 502 towards transducer 512, beads 504 are free to move within the fluidized bed of column 502. As beads 504 approach the acoustic field generated by transducer 512, they are blocked by the acoustic edge effect and/or being trapped in the acoustic field. In any case, beads 504 are prevented from passing to the output of column 502. As target cells 506 bind to beads 504, target cells 506 are prevented from exiting column 502 along with the beads 504 to which they are bound. Nontargeted cells 508 are not influenced as strongly by the acoustic field as are beads 504 and can pass through the acoustic field and exit column 502.

This affinity technique employed with fluidized bed system 500 can be implemented on a single-pass basis. System 500 can be configured with the choice of beads to select for material that passes through and exits column 502, or to select for material that is bound to the beads and retained in column 502. The passed or retained material can be positively or negatively selected.

Figure 6:
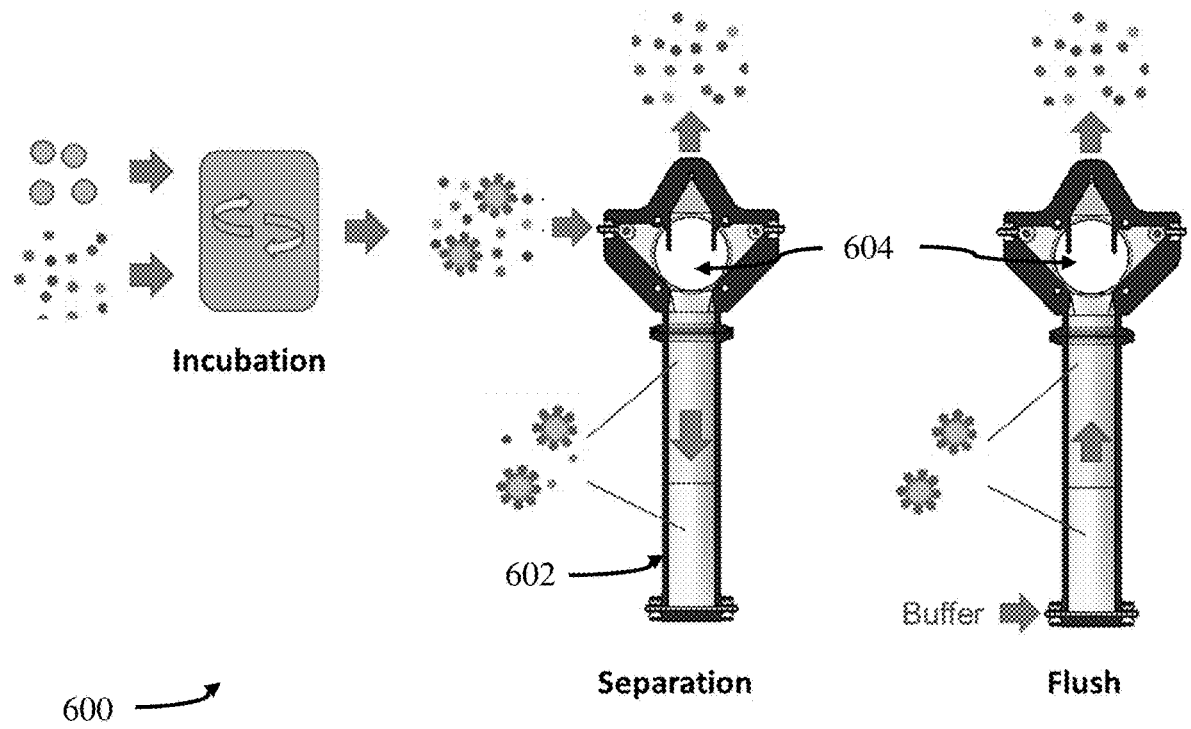
FIG. 6 is a diagram of an acoustic affinity system and process.

Referring to FIG. 6, an affinity separation process 600 is illustrated. Process 600 includes an external incubation step where affinity beads and cells are combined together to obtain bead complexes. The mix of bead complexes and uncombined material in a fluid is fed into a column 602. As the fluid mix travels along column 602, the bead complexes are directed into column 602 by an acoustic field generated by transducer 604. The uncombined material exits column 602 by passing through the acoustic field. This separation step retains the bead complexes while removing a majority of the uncombined material. Once the bead complexes are loaded into column 602, a flush process can be implemented with the introduction of a buffer fluid at the base of column 602. The remaining uncombined material moves with the buffer fluid through the acoustic field generated by transducer 604. The bead complexes also move with the buffer fluid along column 602 but are blocked from exiting by the acoustic field.

Process 600 offers a number of features that are advantageous for affinity separation of materials. For example, binding of target material to the beads can take place externally, which also permits flexible incubation steps. The acoustic separation provides a gentle and high throughput separation process that quickly reduces the amount of uncombined material in mix with bead complexes. For example, the separation process can be completed in less than one hour. Process 600 is also flexibly scalable and can handle processing volumes in the range of about 10 mL to about 1 L. In addition, all types of beads may be used in process 600, providing significant flexibility for unique or custom affinity separation processes.

Figure 7:
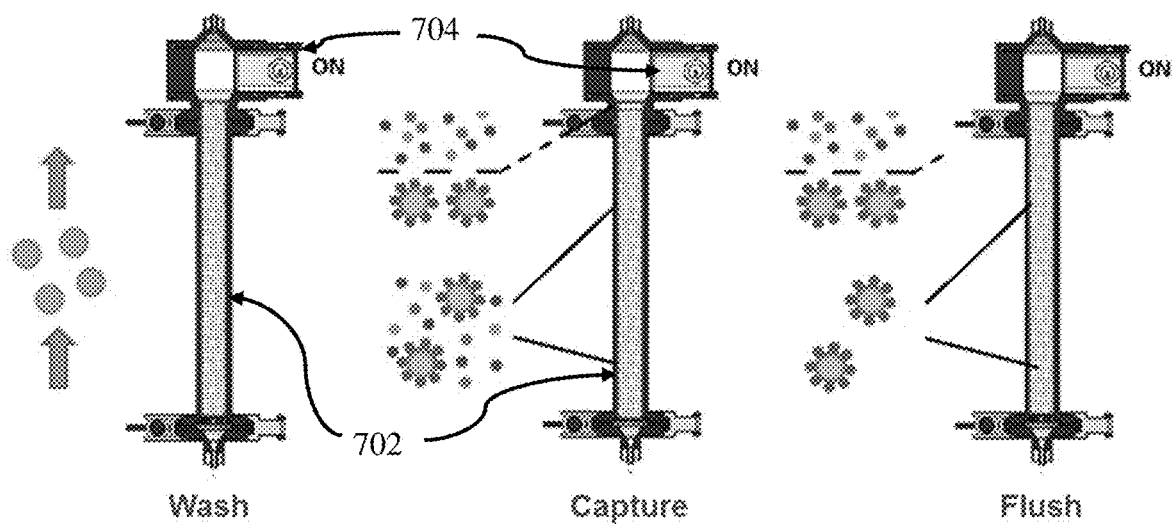
FIG. 7 is a diagram of an acoustic affinity system and process.

Referring to FIG. 7, a fluidized bed system 700 is illustrated. A column 702 is provided, which can be implemented as any of the columns illustrated in FIGS. 4-6. In a first wash process, column 702 is loaded with affinity beads. A wash solution is passed through column 702 while acoustic transducer 704 is on to generate an acoustic field near a top of column 702. The acoustic field retains the affinity beads in column 702 while the wash solution passes through to wash the affinity beads. A capture process is implemented in which cellular material is introduced into column 702. Target cellular material binds to the affinity beads to form bead complexes and is blocked from exiting column 702 by the acoustic field generated by the acoustic transducer 704. Nontargeted material can pass through the acoustic field and can exit column 702. After the capture process, a flush process is provided where fluid is introduced to column 702 to flow the nontargeted material out of column 702. The bead complexes are retained in column 702 against the fluid flow by the acoustic field generated by the acoustic transducer 704.

System 700 offers a number of advantageous features for affinity separation processes, including internal bead binding and low shear forces imposed on the material in column 702.

The internal bead binding with low shear forces can be important when larger beads are used due to potentially greater binding energy that is associated with larger beads. For example, it may take longer, or a greater amount of energy, for targeted cellular material to be captured by the larger beads. Lower shear forces can thus help to avoid impeding binding with larger beads. System 700 can employ acoustic transducer 704 to create an acoustic edge effect, which can lead to improved throughput. For example, the processes of binding and separation can be completed in under 2 hours. System 700 is scalable and can handle processing volumes in the range of about 10 mL to about 1 L. the fluidized bed employed in system 700 can be used with beads or with cells for the purposes of affinity separation and/or separation alone.

Figure 8:
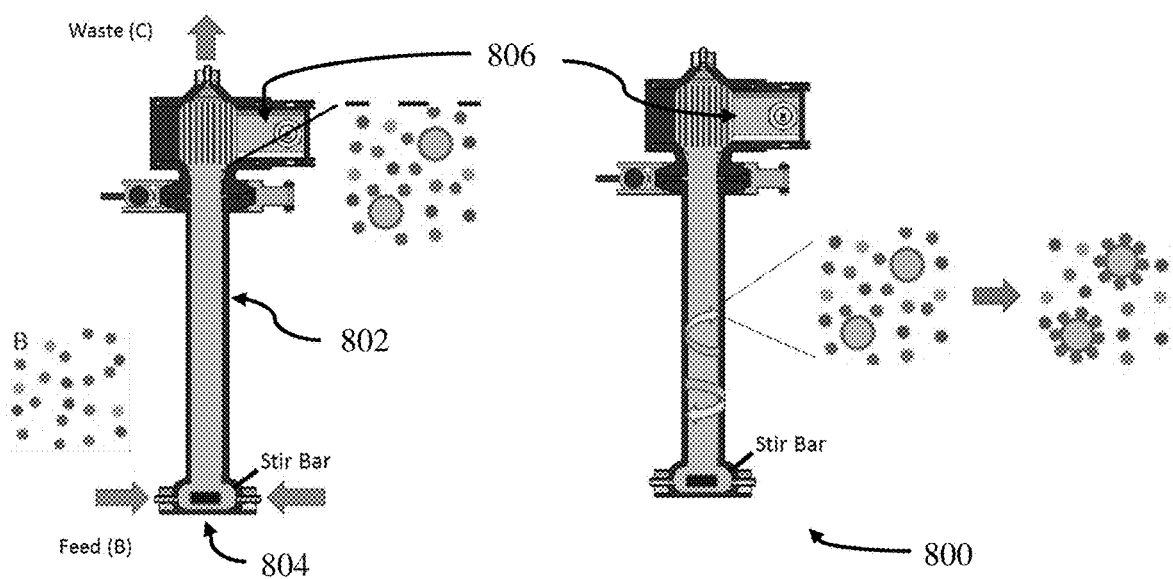
FIG. 8 is a diagram of an acoustic affinity system and process.

Referring to FIG. 8, a cell selection system 800 is illustrated. System 800 includes a column 802 that is provided with a stirring mechanism 804. Stirring mechanism 804 can be implemented as a stir bar near a base of column 802. An affinity separation process can be implemented in system 800 using column 802 as a fluidized bed. Column 802 is loaded with affinity beads, for example in a range of about 10% to about 30% packing. The affinity beads are washed with the introduction of a fluid into column 802 while the acoustic field is generated by acoustic transducer 806. The fluid exits column 802 while the affinity beads are blocked from exiting by the acoustic field. A mix of cellular material is introduced into column 802 while acoustic transducer 806 generates an acoustic field near a top of column 802. All of the cellular material is retained in column 802, along with the affinity beads, with the implementation of the acoustic field. Excess fluid may pass the acoustic field and exit column 802 while the cells and affinity beads are blocked from exiting.

During the wash process and the introduction of the cellular material, transducer 806 may be operated in different modes or with different characteristics to, in one case, block the affinity beads from exiting during the wash process, and in another case, block both of the affinity beads and the cellular material from exiting. For example, the frequency used to drive transducer 806 may be different to retain the affinity beads than the frequency when both the cells and affinity beads are retained.

Once column 802 is loaded with affinity beads and cellular material, stirring mechanism 804 can be employed to agitate column 802. The agitation contributes to moving the affinity beads and the cellular material within column 802. As the affinity beads and cellular material move within column 802 the affinity binding process for targeted material can be enhanced. This incubation step can be implemented with no fluid flow and with transducer 806 being unenergized.

Once the incubation/binding process is completed, the affinity bead/targeted material complexes can be washed, and nontargeted material can be removed from column 802. The targeted material may be separated from the affinity beads with a solution provided to column 802 that promotes detachment of the targeted material from the affinity beads. For example, the solution can include enzymes (e.g., trypsin) in a buffer. For example, The targeted material may then be removed from column 802, while the affinity beads are retained with the acoustic field generated by the acoustic transducer 806.

Figure 9:
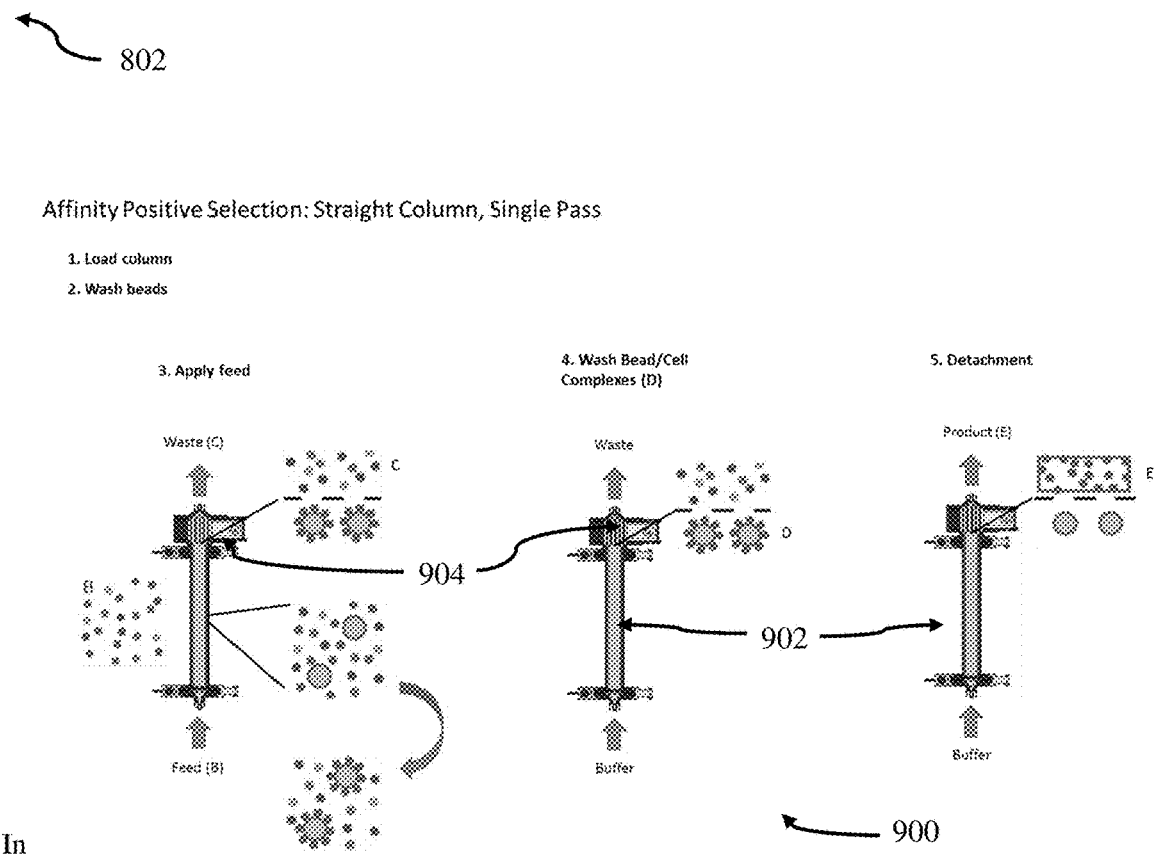
FIG. 9 is a diagram of an affinity positive selection in an acoustic affinity process.

Referring to FIG. 9, an affinity selection process 900 for positive selection in a straight column with a single pass is illustrated. Process 900 begins with the loading of column 902 with affinity beads and washing the beads. Acoustic transducer 904 generates an acoustic field near a top of column 902 during the loading and washing processes. A mix of cellular material is then fed into column 902. Target material is bound to the affinity beads to form bead complexes. The nontargeted material exits column 902 through the acoustic field. The targeted material is retained with affinity beads in column 902, while the nontargeted material exits column 902. The bead complexes are washed with the introduction of a buffer into column 902. A detachment buffer is introduced to column 902 to cause the targeted material to detach from the affinity beads. With the acoustic field in place, the detached targeted material exits column 902 and is collected, while the affinity beads are retained.

Figure 10:
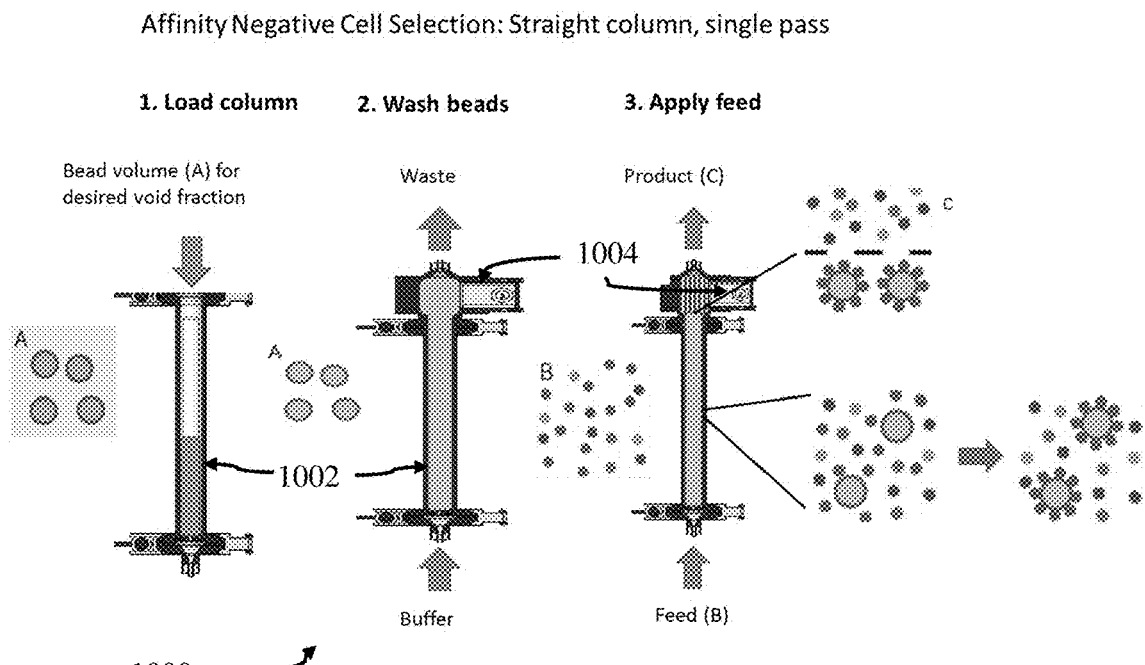
FIG. 10 is a diagram of an affinity negative selection in an acoustic affinity process.

Referring to FIG. 10, an affinity selection process 1000 for negative cell selection in a straight column with a single pass is illustrated. Process 1000 begins with the loading of column 1002 with affinity beads to a desired void fraction. The loading process can be implemented while acoustic transducer 1004 is removed from column 1002. With acoustic transducer 1004 connected to a top of column 1002, the affinity beads are washed with the introduction of a buffer. This washing process also serves to expand the bead volume to form a fluidized bed. With acoustic transducer 1004 generating an acoustic field, a mix of cellular material is fed into column 1002. Target material is bound to the affinity beads to form bead complexes. The nontargeted material exits column 1002 through the acoustic field. The targeted material is retained with the affinity beads in column 1002, while the nontargeted material exits column 1002 and is collected as the desired product. This negative cell selection removes the targeted material from the mix of cellular material in a single pass. The affinity beads can be multiplexed or configured to bind with more than one type of targeted material, which permits multiplexed negative selection in a single pass.

Figure 11:
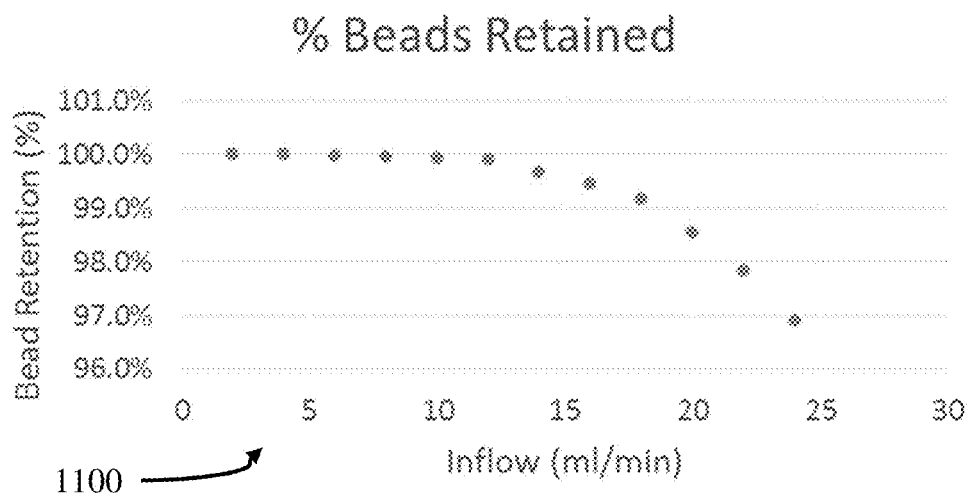
FIG. 11 is a graph showing the retention versus inflow fluid rate.

Referring to FIG. 11, a graph 1100 illustrates bead retention with an acoustic field versus fluid inflow rate for an acoustic fluidized bed column. As shown in graph 1100, 100% of the beads are retained in the column as the fluid inflow rate increases from 0 to about 10 mL per minute. As the fluid inflow rate increases beyond 10 mL per minute, more and more beads pass through the acoustic field. The data presented in graph 1100 is useful to understand the breakthrough fluid inflow rate that causes beads to pass through the acoustic field. This test used SP Sepharose "Fast Flow" beads with an average diameter of 90 um and an average density of 1.033 g/cc. The terminal velocity was 52.2 cm/hr. The column parameters were: volume –40 ml; height –20 cm; and diameter –1.6 cm. The expanded void fraction was 70% with a starting bead concentration of 7.86E+05 cells/ml. Operating parameters were: frequency –1 MHz and power –3 W.

Figure 12:
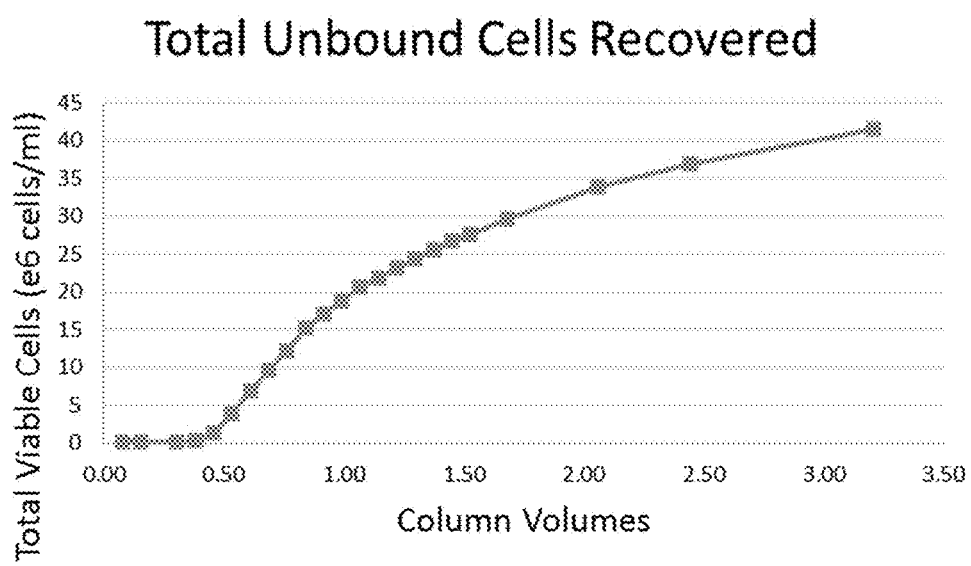
FIG. 12 is a graph showing the cell viability versus column volumes.

Referring to FIG. 12, a graph 1200 illustrates total viable cells recovered in an acoustic affinity system versus column volumes where column volumes indicates the amount of input to the system normalized by the volume of the column. As shown in graph 1200, the total viable cells, in millions of cells per milliliter, increases significantly after about a half a column volume. This data shows the efficiency of binding in the acoustic affinity system. For example, almost no unbound cells are observed during the initial half a column volume of supplying a cellular material feed to the fluidized bed column.

Figure 13:
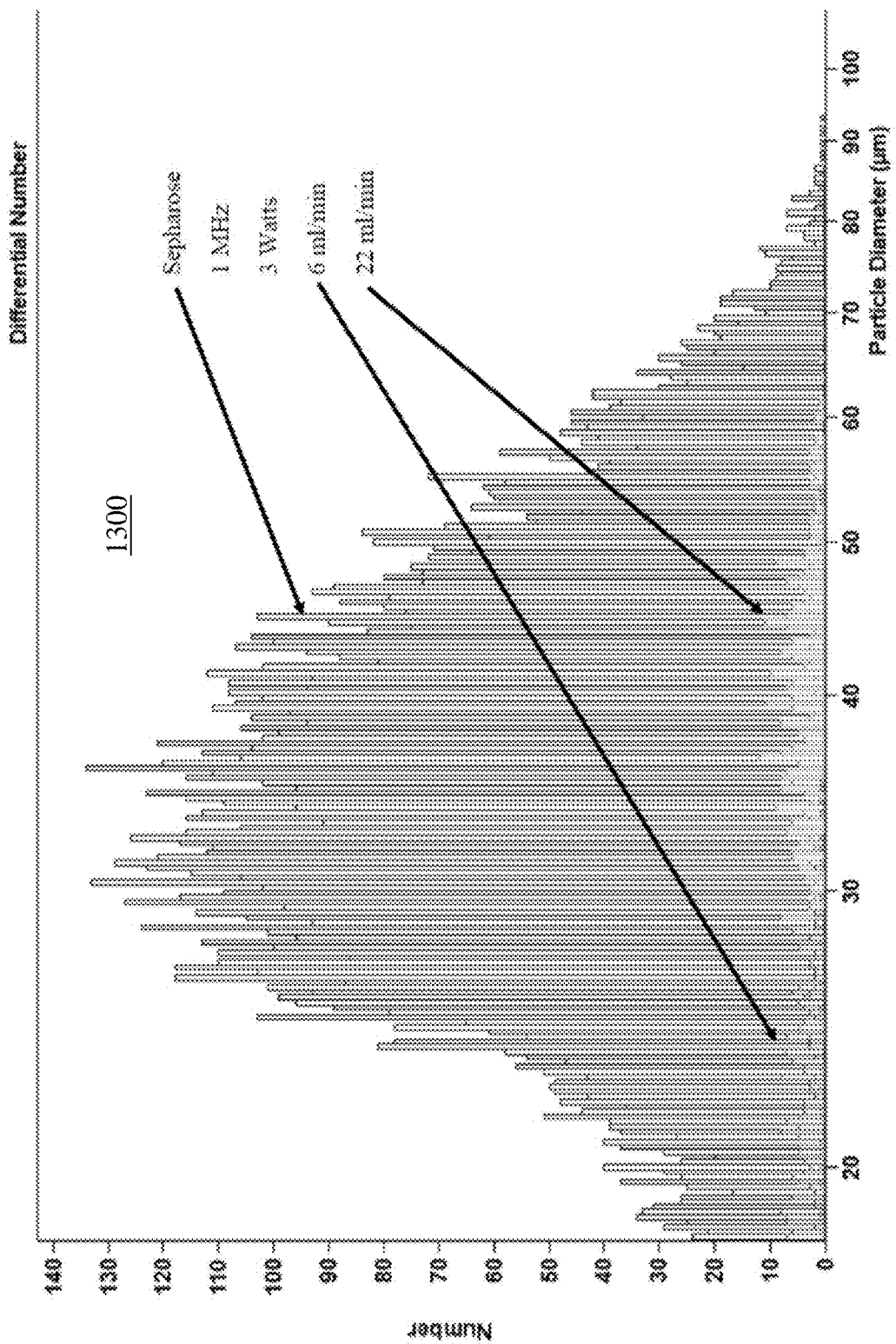
FIG. 13 is a graph showing a histogram of particle sizes.

Referring to FIG. 13, a graph 1300 illustrates a histogram of beads exiting a fluidized bed column in accordance with particle diameter. Graph 1300 shows that at lower flowrates, small particles escape the column while larger particles are retained. In addition, the average size of an escaping particle increases with flow rate.

Figure 14:
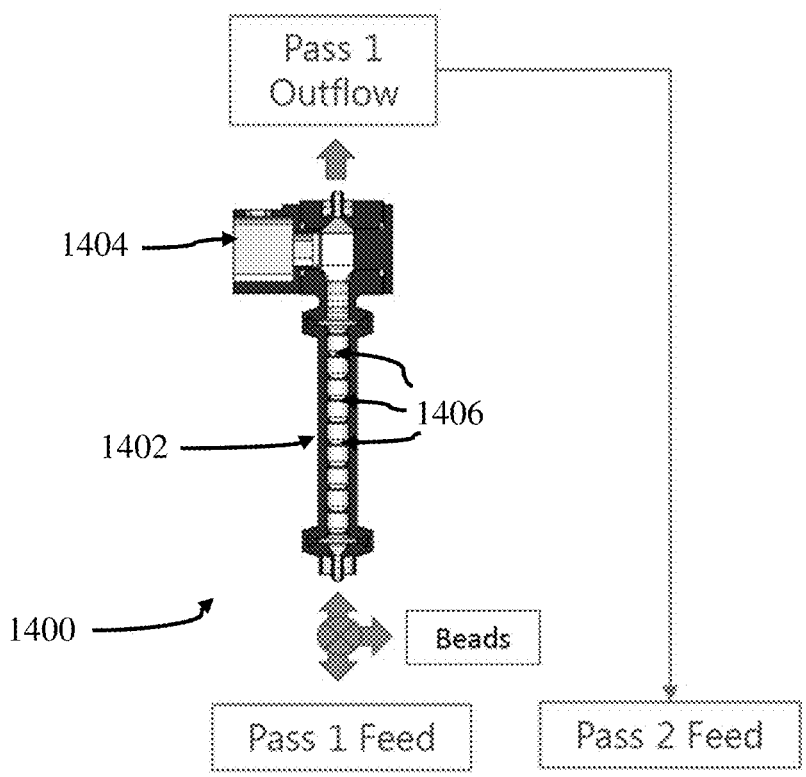
FIG. 14 is a diagram of an acoustic affinity system and process with the recirculation.

Referring to FIG. 14, a fluidized bed system 1400 for implementing acoustic affinity cell selection with the recirculation is illustrated. System 1400 includes a column 1402 and an acoustic transducer 1404. Column 1402 includes annular ribs 1406 that can impede the flow of fluid and force fluid flow toward the center of column 1402. Ribs 1406 can help prevent undesired effects such as channeling within column 1402.

System 1400 is operated similarly to those discussed above. For example, system 1400 may be used for positive or negative selection and can employ different modes of operation with the acoustic transducer 1404. System 1400 illustrates the use of recirculation to improve target cell recovery, by providing more opportunities for target cells to bind with beads in column 1402. After the beads are loaded into column 1402 and washed, a pass 1 feed is supplied to column 1402. The outflow of column 1402 resulting from the pass 1 feed is collected for use as a pass 2 feed. The pass 2 feed is used as the input for a feed supply in a follow-on recirculation pass. Although not shown, the pass 2 feed can generate an outflow that can be collected for another follow-on recirculation pass. Any number of recirculations can be employed. Each of the example systems and fluidized beds discussed herein can be configured to have multiple recirculation passes.

Figure 15:
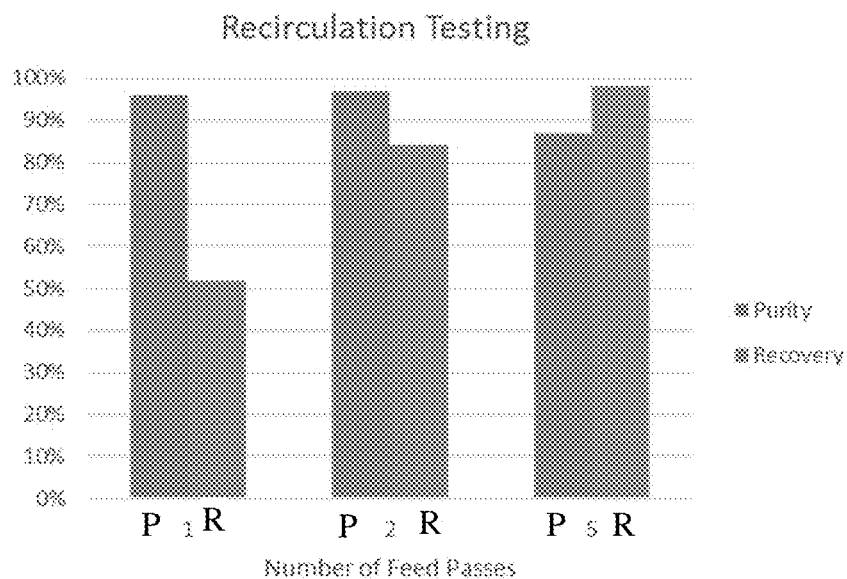
FIG. 15 is a bar graph showing purity and recovery in a recirculation arrangement.

Referring to FIG. 15, a graph 1500 illustrates the purity (P) and percentage recovery (R) in a fluidized bed system with a number of recirculated feed passes. Graph 1500 shows that purity is maintained at a high level, greater than 90% for recirculation passes 1 and 2, and greater than 80% for recirculation pass 3. The recovery of cells increases with each recirculation pass, nearing 100% with the third recirculation.

Figure 16:
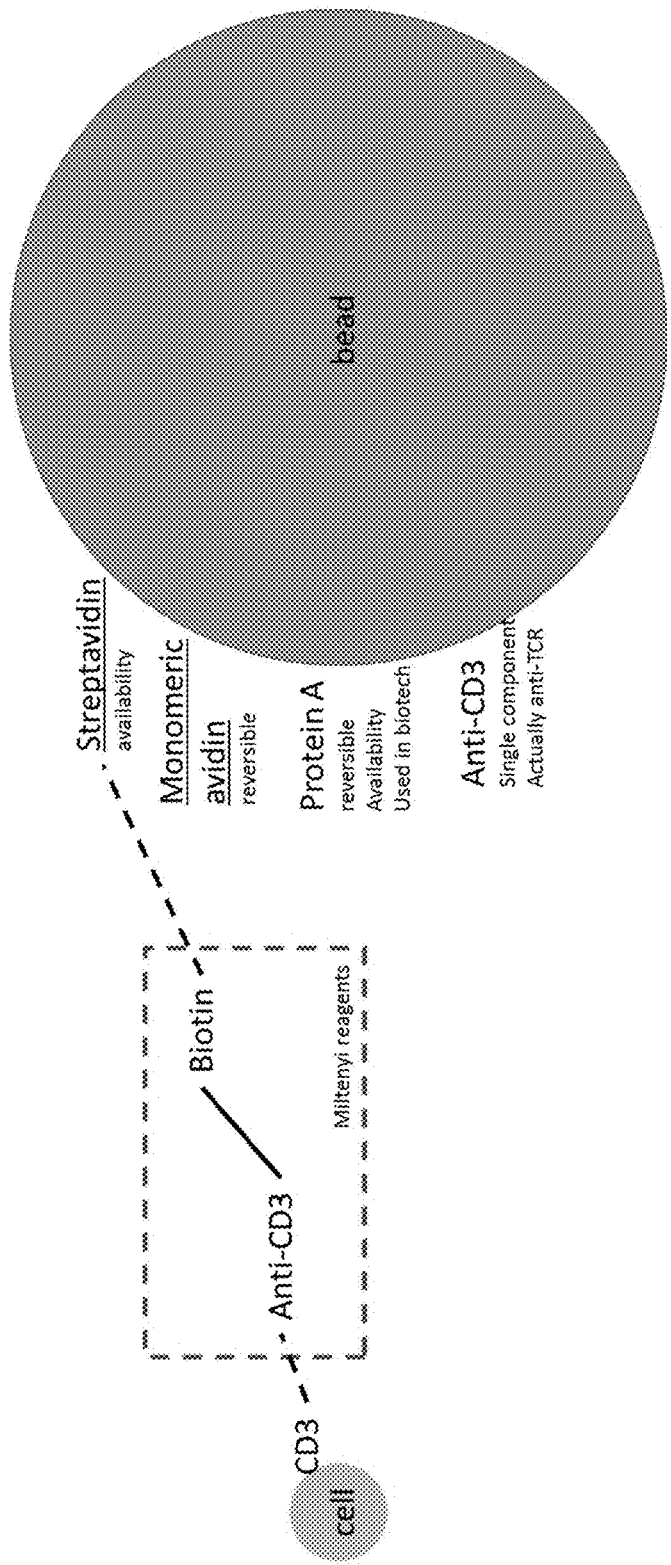
FIG. 16 is a diagram of a bead with functionalized material for targeting a CD3 marker.

Referring to FIG. 16, an example implementation of a bead with the functionalized material is illustrated. The bead is configured to have an affinity for CD3 receptors on a cell. The bead may be coated with streptavidin, monomeric avidin, protein A, and/or anti-CD3. A biotin-anti-CD3 complex may be used to provide the affinity target for the CD3 receptor on the cell. The anti-CD3-biotin antibody may be replaced or substituted with an anti-TCR-biotin antibody. The streptavidin coated beads can provide a greater binding surface area than other types of coatings. For example, the streptavidin coated beads can have a greater cell binding/$cm^2$ ratio than other coatings. The term coating is used to refer to functionalized material on a surface of a bead, and may cover portions or all of a bead surface. Alternatively, or in addition, a portion of a bead may be coated with streptavidin and another portion may be coated with another functionalized material to implement multiplexed affinity processes.

Figure 17:
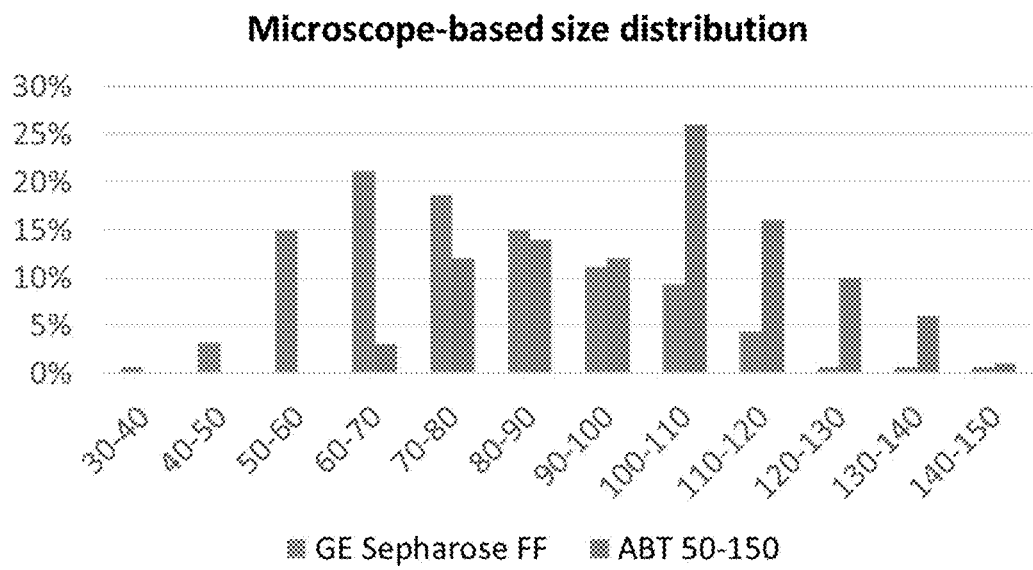
FIG. 17 is a graph showing size distributions of different types of beads.

Referring to FIG. 17, a graph showing size distributions of different types of beads is illustrated. The y-axis is graduated in terms of percentage, while the x-axis is graduated by size in micrometers. The graph illustrates the different size distributions of the GE Sepharose beads and the ABT beads. The beads are distributed over a size that is greater than the size of the cells. The size differential between the beads on the cells can be used as an acoustic contrast factor to distinguish between and separate the beads and the cells.

Figure 18:
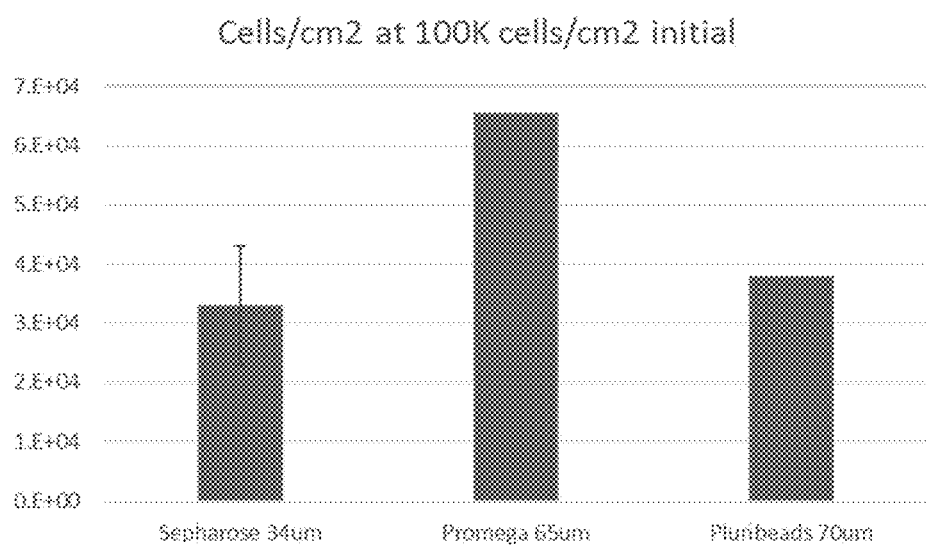
FIG. 18 is a graph showing binding ratios for different types of beads.

Referring to FIG. 18, a graph illustrates binding ratios for different types of beads. The binding ratios are for an initial cell population of 100,000 cells. The y-axis represents cells/$cm^2$ and the x-axis represents the different types of beads. As illustrated, the Sepharose beads, with an average size of 34 μm in diameter, attained a binding ratio of greater than 30,000 cells/ $cm^2$. The Promega beads, with an average size of 65 μm in diameter, attained a binding ratio of about 65,000 cells/ $cm^2$. The Pluribeads, with an average size of 70 μm in diameter, attained a binding ratio greater than the Sepharose beads, and less than 40,000 cells/ $cm^2$.

Figure 19:
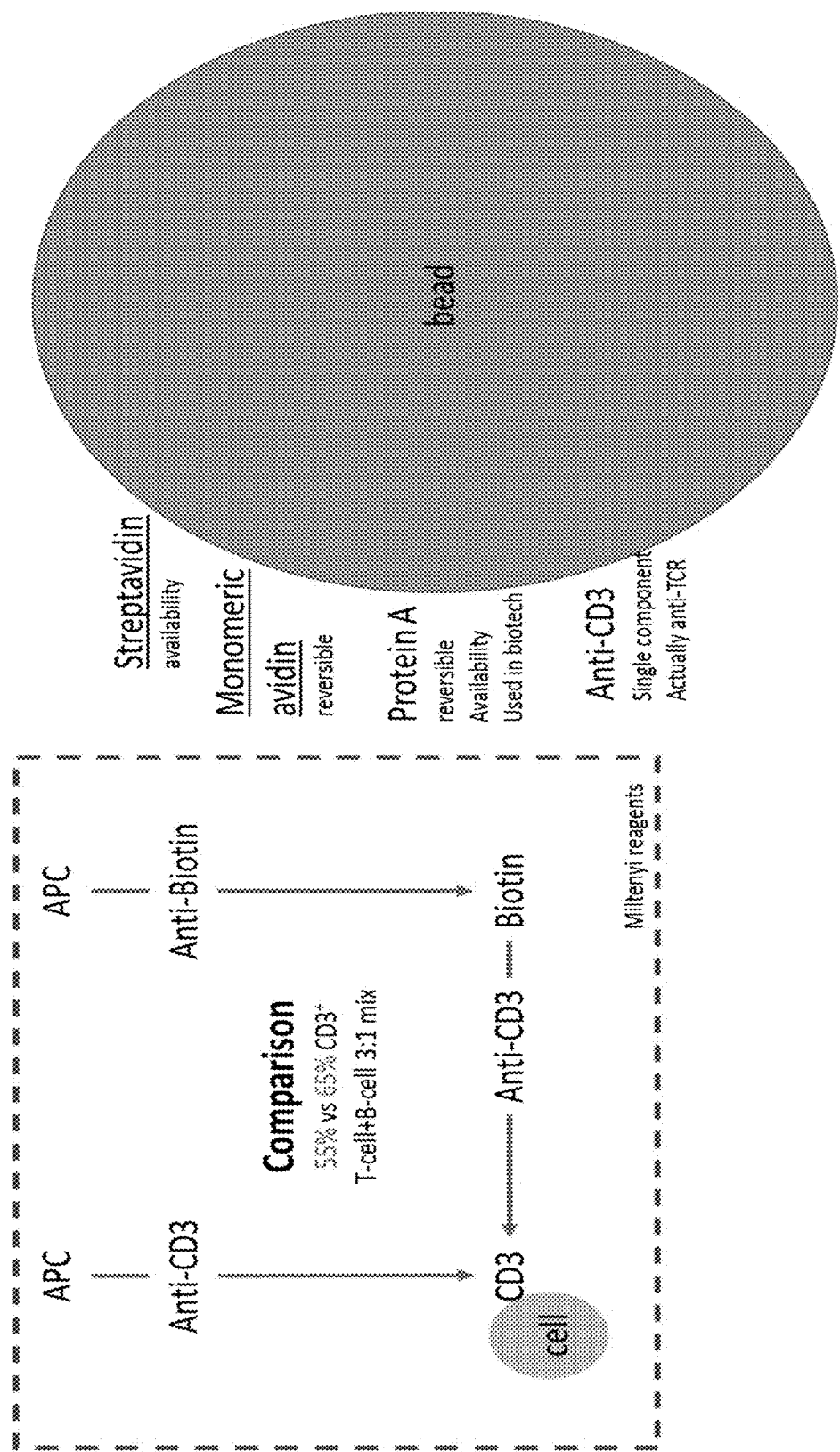
FIG. 19 is a diagram showing a comparative analysis between different affinity systems.

Referring to FIG. 19, a diagram illustrating a comparative analysis between different affinity systems is shown. One system uses APC and anti-CD3, while the other system uses APC, anti-biotin, biotin, and anti-CD3. As shown in the diagram, the system including the biotin resulted in about 65% binding, while the system without biotin resulted in about 55% binding. The comparative implementation includes antiCD3-fluorophore vs. antiCD3-biotin+antibiotin-fluorophore.

Figure 20:
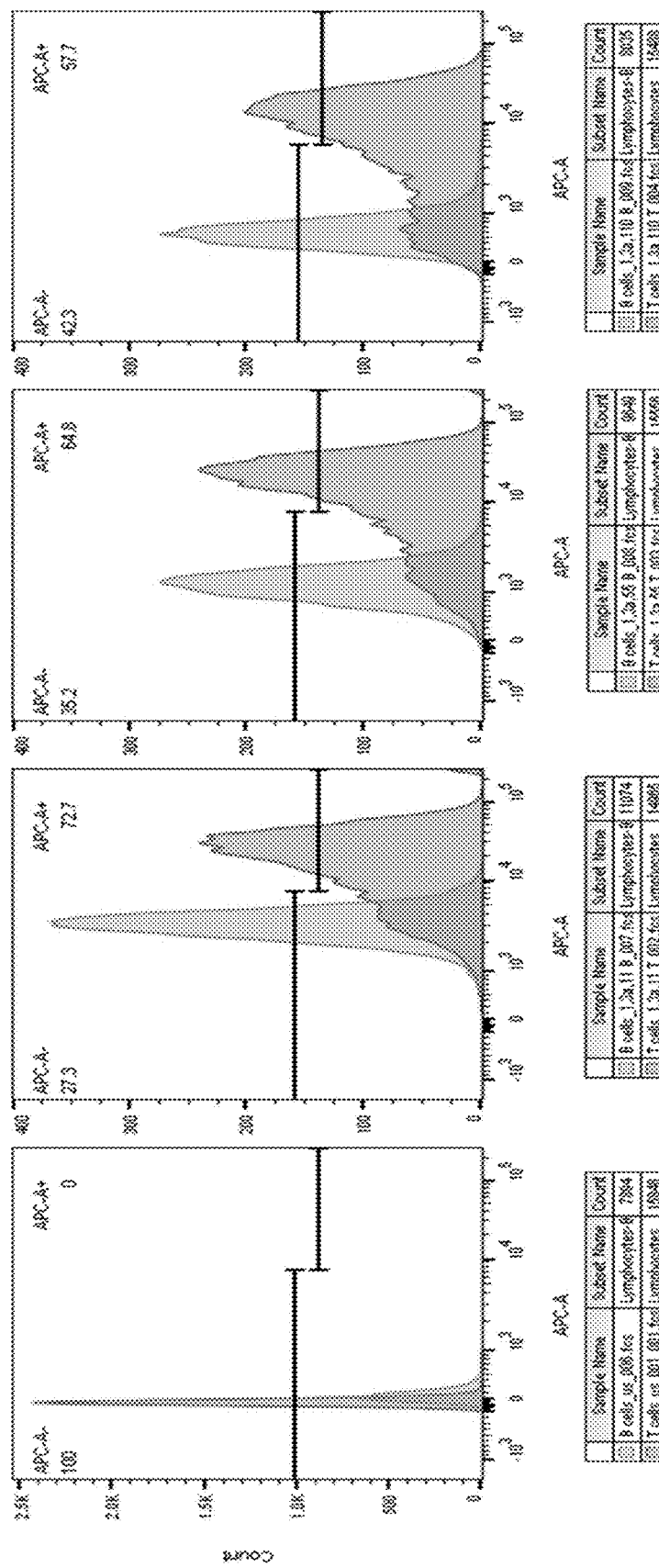
FIG. 20 shows four graphs illustrating cell population differences with changes in antibody titration ratios.

Referring to FIG. 20, several graphs are illustrated representing cell count for different antibody titration ratios. As the graphs illustrate, the cell populations have greater separation as the titration ratio increases.

Figure 21:
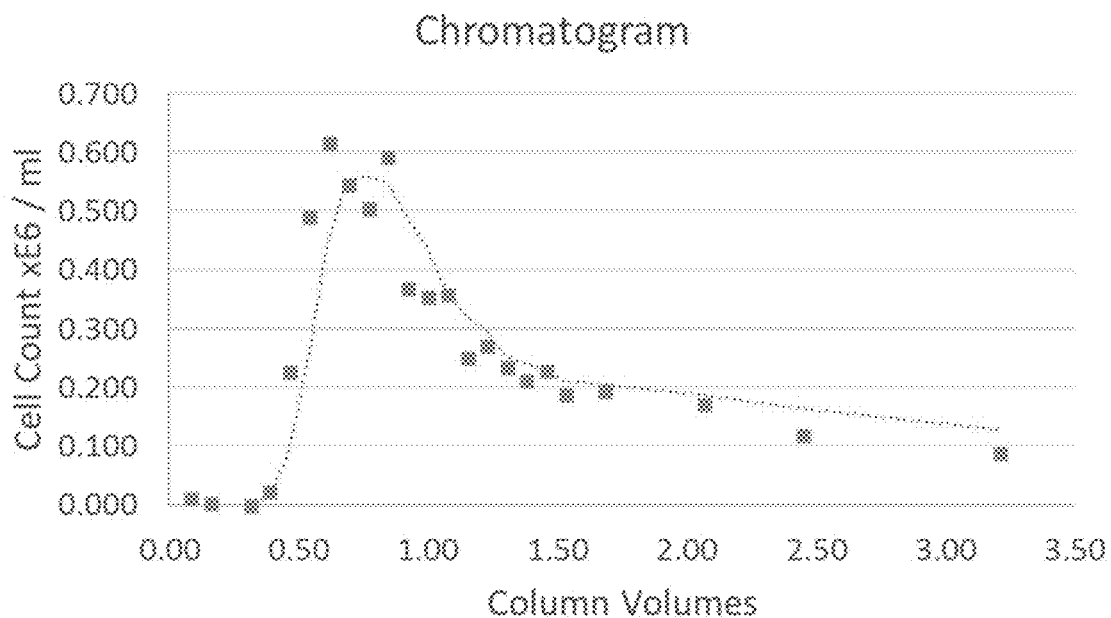
FIG. 21 is a chromatogram showing cell count per milliliter versus column volumes.

Referring to FIG. 21, a chromatogram illustrating cell count per milliliter versus column volumes is shown. Column volumes referred to the amount of fluid entrained with material that is presented to or recirculated in a fluidized bed. It is desirable in the fluid flow through the column to achieve plug flow.

Figure 22:
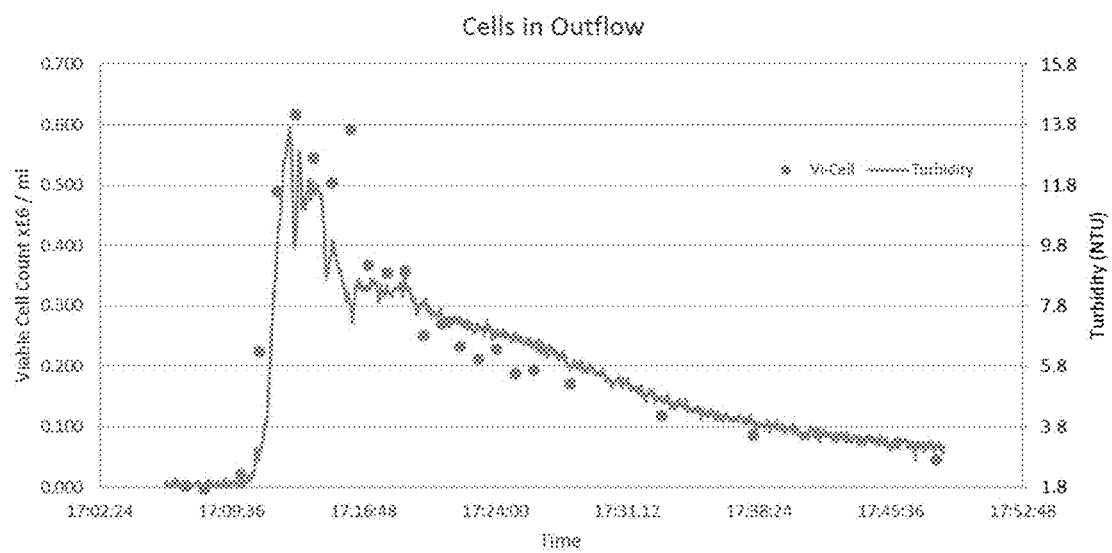
FIG. 22 is a graph showing cell count in column outflow over time.

Referring to FIG. 22, a graph illustrating cell count in column outflow over time is shown. Turbidity of the column outflow correlates well with cell concentration.

Several experimental tests for acoustic affinity cell separation were conducted. The results of the tests are tabulated as examples below.

EXAMPLE 1

Four fluidized bed platform tests were performed with different cell concentrations (100 e6/mL and 10 e6/mL) and different capturing antibody combinations (Anti-TCR a/b only vs Anti-TCR a/b and Anti-CD52) on the first day of testing. The initial feed concentration (100 e6/mL and TCR a/b-population was 74-78%).

All samples were incubated with the corresponding capturing antibody combinations listed in Table 1 in 2% BSA in PBS for 20 minutes on the IKA roller (30 rpm). Cells were washed twice with 2% BSA in PBS and finally re-suspended in 10 mL 2% BSA in PBS. A sample was removed for flow cytometry and used as the initial population for tests A through D. Next, 4 ml of a 50% solid Promega bead slurry were loaded into the fluidized bed column and washed with 30 ml of a 2% BSA in PBS solution to remove residual ethanol and particulates. This initial washing step was performed at a flow rate and power of 1 ml/min and 0.75 W.

The feed cell population was then separated using the fluidized bed unit packed with avidin-conjugated methacrylate beads (Promega) which operated at the following conditions; flow rate ~1 mL/min and power ~0.75 W. The first fraction, denoted as the outflow, was collected after the entire sample was loaded into the fluidized bed. A second fraction, denoted as the flush, was collected after flushing the fluidized bed with 30 ml of a 2% BSA in PBS solution at 1 ml/min and 0.75 W. This flushing step is implemented to ensure all uncaptured cells are recovered. Once this process was completed, the remaining contents of the column were retrieved and collected as the third fraction, denoted as the holdup. Samples from all three fractions were collected for flow cytometry. For the purposes of conducting a mass balance, the mass and cell count for each fraction was recorded.

TABLE 1

Fluidized Bed (FB) platform test parameters
Day 1, Fluidized Bed (FB) test parameters

| Label | Antibody | Bead | Cell conc. [×10^6/ mL] | Sample volume [mL] | Total cell # [×10^6] | Bead volume [mL] | TCR a/b [mL] | CD52 [mL] | Analytics |
|---|---|---|---|---|---|---|---|---|---|
| FB_A | TCR a/b | Promega | 100 | 10 | 1000 | 2 | 1.5 | — | Counting & Flow |
| FB_B | TCR a/b and CD52 | Promega | 100 | 10 | 1000 | 2 | 1.5 | 0.56 | Counting & Flow |
| FB_C | TCR a/b | Promega | 10 | 10 | 100 | 2 | 0.15 | — | Counting & Flow |
| FB_D | TCR a/b and CD52 | Promega | 10 | 10 | 100 | 2 | 0.15 | 0.056 | Counting & Flow |

The purity increased by approximately 15% for all samples after separation by the fluidized bed unit, where the initial cell population consisted of 76% TCR knockout cells. In tests conducted at a higher cell concentration (100E6 cells/mL), samples A and B yielded a purity of 13% and 10% in the outflow and 11% and 8% in the flush respectively showing a slight decrease in purity in the second fraction. The purity in the holdup fraction was 73.2% and 68.1% for samples A and B indicating that 100% purity was not achieved. Tests conducted at lower cell concentrations (10E6 cells/mL) yielded a higher purity of 90.5% and 92.4% in the outflow fraction and even higher purity in the flush fraction of 94.8% and 93.2% in samples C and D respectively. This result showed that lower cell concentrations were better with current conditions used with the fluidized bed unit. Overall employing the combination of anti-TCR and anti-CD52 as capturing antibodies did not yield significantly different purity compared to using anti-TCR as the sole capturing antibody.

TABLE 2

TCR a/b− purity and recovery from Fluidized Bed test
Day 1, Fluidized Bed (FB) test results

| | TCR a/b− purity [%] | | | | Recovery [%] |
|---|---|---|---|---|---|
| Label | Control | Outflow | Flush | Hold-up | |
| FB_A | 74.50% | 84.10% | 83.10% | 73.00% | 6.70% |
| FB_B | 75.40% | 83.10% | 81.90% | 67.50% | 4.80% |
| FB_C | 78.10% | 90.50% | 94.80% | 78.40% | 33.50% |
| FB_D | 76.30% | 92.30% | 93.20% | 81.30% | 32.90% |

The total TCR− recovery for each test is equal to the sum of TCR− cells in the flow-through and flush fractions divided by the starting TCR− cell count (See Eq. 6 in Appendix). There are two mechanisms by which TCR-cells could be retained in the fluidized bed system: acoustic retention and inefficient flushing. Acoustic retention occurs when a free cell experiences a greater force from the acoustic field compared to the drag force exerted by the fluid flow. This happens at high power to flow rate ratios and can be prevented by optimizing operating conditions. Cells also tend to disperse into the volume of the system, making a flush step necessary to improve recovery. The flushing step should have a uniform velocity distribution, otherwise a large volume of buffer is needed to recover TCR− cells as the incoming wash buffer mixes with the fluidized bed. This type of cell retention can be reduced by increasing flush velocity and volume and improving the fluidized bed inlet design.

For each fluidized bed test the total TCR− cell recovery can be seen in Table 2.

The lowest recoveries were seen while testing high cell densities (100 e6/ml). Tests A and B had TCR− recoveries of 7% and 5% respectively. A "clogging" effect in the column was observed during these tests where beads and cells agglomerated together in very large clumps. Rather than acting as a fluid these solid clumps caused channeling in the column and prevented cells from escaping. It is also possible that non-specific binding occurred as the column fouled.

Tests C and D had similar recoveries, 34% and 33%. The two tests with 10 e6/ml behaved as expected but still had relatively low TCR− cell recoveries. This is due to the low fluid velocity and inefficient flush step described previously and can be improved by optimizing operating conditions and improving the fluidized bed inlet design. Changing the antibody had a minimal effect on cell recovery.

EXAMPLE 2

Four Acoustic Separator unit tests were performed with different affinity bead types (Promega, Dynabead, PolyStyrene 6 um and 14 um). On Day 2, fixed antibody combination (Anti-TCR and Anti-CD52) and antibody volume of 0.15 mL and 0.052 mL, respectively) were used. The initial TCR a/b-population was 77%.

All samples were incubated with anti-TCR and anti-CD52 in 2% BSA in PBS for 20 minutes on the IKA roller (30 rpm). Cells were washed twice with 2% BSA in PBS. A sample was removed for flow cytometry and used as the initial population for tests L through Q. Samples were incubated with the corresponding bead candidate listed in Table 3. for 30 minutes on the IKA roller (30 rpm) in 10 mL of 2% BSA in PBS and then separated using the Acoustic Separator unit operated at the following conditions; flow rate ~1 mL/min and power ~0.75W. The first fraction, denoted as the outflow was collected after the entire sample passed through the acoustic field. A second fraction denoted as the flush was collected after flushing the fluidized bed with 30 ml of a 2% BSA in PBS solution. Once this process was completed, the remaining contents of the column were retrieved and collected as the third fraction, denoted as the holdup. Samples from all three fractions were collected for flow cytometry. For the purposes of conducting a mass balance, the mass and cell count for each fraction was recorded.

TABLE 3

Acoustic Separator(AC) platform test parameters
Day 2, Acoustic Separator (AC) parameters

| Label | Antibody | Bead | Cell conc. [×10^6/mL] | Sample volume [mL] | Total cell # [×10^6] | Bead volume [mL] | TCR a/b [mL] | CD52 [mL] | Analytics |
|---|---|---|---|---|---|---|---|---|---|
| AC_A | TCR a/b and CD52 | Promega | 10 | 10 | 100 | 2 | 0.15 | 0.056 | Counting & Flow |
| AC_B | TCR a/b and CD52 | Dynabead | 10 | 10 | 100 | 0.015 | 0.15 | 0.056 | Counting & Flow |
| AC_C | TCR a/b and CD52 | PS (6 um) | 10 | 10 | 100 | 0.015 | 0.15 | 0.056 | Counting & Flow |
| AC_D | TCR a/b and CD52 | PS (14 um) | 10 | 10 | 100 | 0.015 | 0.15 | 0.056 | Counting & Flow |

The purity increased by approximately 13% for all samples after separation by the Acoustic Separator unit, where the initial cell population consisted of 77% TCR knockout cells. The sample incubated with Dyna beads resulted in the highest purity of 89.4% in the outflow fraction while the sample incubated with Polystyrene (10-14 µm) beads resulted in the lowest purity of 84.3%. This trend was also observed in the flush fraction where samples incubated with Dyna beads yielded 91.1% purity and Polystyrene beads yielded 84.5% purity. The purity in all samples increased slightly from the outflow (84.3%-89.8%) to the flush fraction (84.6%-91.1%).

TABLE 4

TCR a/b− purity and recovery from Fluidized Bed test
Day 2, Acoustic Separator (AC) test results

| | TCR a/b− purity [%] | | | Recovery [%] |
|---|---|---|---|---|
| Label | Control | Outflow | Flush | Hold-up | |
| AC_A | 76.20% | 85.70% | 86.20% | 79.20% | 79.90% |
| AC_B | 77.60% | 89.80% | 91.10% | 88.90% | 17.00% |
| AC_C | 77.70% | 88.30% | 89.40% | 84.70% | 26.20% |
| AC_D | 77.40% | 84.30% | 84.60% | 79.70% | 27.10% |

The total TCR− cell recoveries for each acoustic separator system test can be seen in Table 4. In this figure it appears that the recovery is affected by the bead type, with 50 um Promega beads having an 80% TCR− cell recovery and 4.5 um Dyna-beads having just 17% recovery. Both polystyrene particles had similar recoveries, 26% and 27% for 6 um and 14 um beads respectively. Since every test was performed with the same operating conditions, similar recoveries were expected so this relationship should be confirmed in future work. Like in the fluidized bed, TCR− recovery in the Acoustic Separator system can be increased by increasing flow velocity and by improving the inlet and collector designs.

EXAMPLE 3

Two Fluidized Bed (FB) processes and two Acoustic Separator(AS) processes were performed. Different pump systems (Syringe pump and peristaltic pump) were tested on the Fluidized Bed unit and two new bead candidates were tested on the Acoustic Separator unit on the first day of testing. The initial feed concentration was $10^7$ cells/mL and TCR a/b-population was about 80%.

Sample preparation and acoustic unit operating procedures were the same as previous examples. Briefly, feed samples for the Fluidized Bed were incubated with biotinylated anti-TCR a/b antibody (Table 5) in 2% BSA in PBS for 20 minutes on the IKA roller (30 rpm). Cells were washed twice with 2% BSA in PBS and finally re-suspended in 10 mL 2% BSA in PBS. For the feed samples for the Acoustic Separator unit, bead incubation was followed by antibody-cell incubation. $1\times10^6$ cells from each feed sample were collected separately for flow cytometry and used as the initial population for each test.

The fluidized bed column was loaded with 2 ml Promega bead slurry (avidin-conjugated methacrylate beads) and then washed with 30 ml of a 2% BSA in PBS solution to remove residual ethanol and particulates. This initial washing step was performed at 3 mL/min and 2.25 W. Two different pumps (Syringe pump—FB_A and Peristaltic pump—FB_B) were evaluated on day 1. The feed cell population was then separated using the fluidized bed unit packed with Promega beads which operated at 3 mL/min and 4 mL column volume. For the Acoustic Separator unit operation, bead labeled feed were separated at the following conditions; flow rate −1mL/min and power −0.75W.

For the performance evaluation, processed samples from both units were collected and analyzed from three different fractions—outflow, flush and holdup (Table 6). The first fraction of the processed sample, denoted as the outflow, was collected after the entire sample was loaded into the fluidized bed. A second fraction, denoted as the flush, was collected after flushing the fluidized bed with 30 ml of 2% BSA in PBS solution. This flushing step is necessary to ensure all uncaptured cells are recovered. Once this process was completed the remaining contents of the column were retrieved and collected as the third fraction, denoted as the holdup. Samples from all three fractions were collected for flow cytometry. The mass and cell concentration count for each fraction was recorded for the cell recovery evaluation.

TABLE 5

Fluidized Bed(FB) and Acoustic Separator (AS) unit test parameters (bead volume = 1 cc, slurry volume = 4 ml.
Day 1, Fluidized Bed (FB) and Acoustic Separator (AS) test, parameters

| Label | Antibody | Bead | Cell conc. [×10^6/mL] | Feed volume [mL] | Bead volume [mL] | TCR a/b [mL] | Power [W] | Flow rate [mL/min] | Comments |
|---|---|---|---|---|---|---|---|---|---|
| FB_A | Anti-TCR | Promega | 10 | 10 | 2 | 0.15 | 2.25 | 3 | Syringe pump |
| FB_B | Anti-TCR | Promega | 10 | 10 | 2 | 0.15 | 2.25 | 3 | Peristaltic pump |

TABLE 5-continued

Fluidized Bed(FB) and Acoustic Separator (AS) unit test parameters (bead volume = 1 cc, slurry volume = 4 ml.
Day 1, Fluidized Bed (FB) and Acoustic Separator (AS) test, parameters

| Label | Antibody | Bead | Cell conc. [×10^6/ mL] | Feed volume [mL] | Bead volume [mL] | TCR a/b [mL] | Power [W] | Flow rate [mL/min] | Comments |
|---|---|---|---|---|---|---|---|---|---|
| AS_C | Anti-TCR | PLGA | 10 | 10 | 0.15 | 0.15 | 0.75 | 1 | Syringe pump |
| AS_D | Anti-TCR | WAX | 10 | 10 | 0.15 | 0.15 | 0.75 | 1 | Syringe pump |

The purity increased by approximately 11~12% for all samples after separation by the Fluidized Bed unit and almost no change after separation by the Acoustic Separator unit, where the initial cell population consisted of 80% TCR knockout cells (Table 6). For the Fluidized Bed tests, both peristaltic pump(FB_A) and syringe pump(FB_B) resulted in similar level of purity (90~92%) in the flow through and flush fraction. In addition to fluidized bed testing, two different micron sized bio-degradable particle candidates (AS_A—PLGA and AS_B—Wax) were tested in Acoustic Separator unit.

Table 6 also shows recovery results. Fluidized Bed with peristaltic pump (FB_A) and syringe pump (FB_B) showed 78% and 61% of TCR– recovery, respectively. Based on the results, FDS decided to use peristaltic pump for upcoming platform validation. Peristaltic pump enables flexibility of further process optimization and closed system development. Acoustic Separator for PLGA and Wax resulted low recovery (50% and 38%, respectively).

The same procedure was performed for feed and initial bead loading of the Fluidized Bed unit as in day 1. Table 7 shows four different operation procedures, no recirculation (FB_E, no recirc.), one recirculation (FB_F, 1 recirc.), 4 recirculations (FB_G, 4 recirc.) and stop and flow (FB_H, Stop and Flow). Specifically, in the stop and flow condition, 2.5 mL of feed samples were loaded with (3 mL/min) and flow stopped for 3 min 20 sec. This procedure was repeated until all the feed volume was loaded into the column. All the feed cells were held in the column by higher power condition (4.5 W) for a total of 13 min 20 sec. Once the recirculation steps and stop and flow steps were finished, the column was flushed with 30 mL of 2% BSA solution. The processed samples were collected and analyzed as in day 1.

TABLE 7

Fluidized Bed (FB) platform and Acoustic Separator (AS) unit test parameters (bead volume = 1 ml)
Day 2, Fluidized Bed (FB) test, parameters

| Label | Antibody | Bead | Cell conc. [×10^6/ mL] | Feed volume [mL] | Bead volume [mL] | TCR a/b [mL] | Power [W] | Flow rate [mL/min] | Comments |
|---|---|---|---|---|---|---|---|---|---|
| FB_E | TCR | Promega | 10 | 10 | 2 | 0.15 | 2.25 | 3 | No recirc. |
| FB_F | TCR | Promega | 10 | 10 | 2 | 0.15 | 2.25 | 3 | 1 recirc. |
| FB_G | TCR | Promega | 10 | 10 | 2 | 0.15 | 2.25 | 3 | 4 recirc. |
| FB_H | TCR | Promega | 10 | 10 | 2 | 0.15 | 2.25 | 3 | Stop and Flow |

The purity increased by approximately 9-18% for all samples after separation, where the initial cell population consisted of 80% TCR knockout cells (Table 8). One recirculation (FB_F) resulted 95.6% and 97.7% of purity in Flow through and Flush portion, respectively. Notably, 4 recirculations (FB_G) showed low purity and we observed some temperature increase due to the 4 times of recirculation. The temperature rising also happened in stop and flow condition (FB_H).

TABLE 6

Fluidized Bed(FB) and Acoustic Separator (AS) unit test parameters
Day 1, Fluidized Bed (FB) and Acoustic Separator (AS) test, results

| | Processed TCR a/b– [%] | | | Recovery |
|---|---|---|---|---|
| Label | Control | Flow through | Flush | Hold-up | [%] |
| FB_A | 80.20% | 92.24% | 91.44% | 86.90% | 78.04% |
| FB_B | 79.10% | 90.43% | 91.26% | 73.20% | 61.37% |
| AS_A | 80.00% | 80.40% | 80.10% | 79.50% | 49.54% |
| AS_B | 80.60% | 81.00% | 83.70% | 79.70% | 38.49% |

EXAMPLE 4

Four fluidized bed unit tests were performed with different operation procedures. The residence time of feed cells in the column was increased by re-circulation of the processed sample or by holding samples in the column for a longer time period. The initial feed concentration was $10^7$ cells/mL and TCR a/b-population was about 80%.

TABLE 8

TCR a/b– purity and recovery from
Fluidized Bed and Acoustic Separator test
Day 2, Fluidized Bed (FB) test, results

| | Processed TCR a/b– [%] | | | Recovery |
|---|---|---|---|---|
| Label | Control | Flow through | Flush | Hold-up | [%] |
| FB_E | 80.50% | 93.16% | 96.37% | 73.50% | 51.86% |
| FB_F | 79.80% | 95.64% | 97.69% | 59.20% | 82.64% |
| FB_G | 80.50% | 89.50% | 84.80% | 56.10% | 98.89% |
| FB_H | 80.10% | 95.11% | 91.51% | 73.30% | 85.75% |

For the TCR a/b– recovery, Recirculation and Stop and Flow condition showed good results. Adding more recirculation steps showed better recovery (one recirc. –82.64% and 4 recirc. 98.89%) and stop and flow condition also resulted high recovery (85.75%).

In accordance with the present disclosure, an acoustic affinity system is discussed that provides a number of advantageous features. For example, the systems and methods discussed herein can provide increased recovery and purity for target cellular material. The systems and methods are scalable, capable of handling a relatively wide range of material volumes. Positive and negative selection can be implemented in accordance with the present disclosure. Positive selection can include implementations with apheresis products. Negative and positive selection can be implemented on a multiplexed basis, where multiple types of cellular material can be selected in one pass. The systems and processes discussed herein can be fully automated and can be figured to be used with consumable components. The acoustic affinity cell selection system can be integrated with a cellular concentrate-wash device and/or system for downstream applications.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known processes, structures, and techniques have been shown without unnecessary detail to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the spirit of the disclosure. For example, the above elements may be components of a larger system, wherein other structures or processes may take precedence over or otherwise modify the application of the invention. Also, a number of operations may be undertaken before, during, or after the above elements are considered. Accordingly, the above description does not bound the scope of the claims.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

What is claimed is:

1. A separation system, comprising:
   a vertically oriented column oriented column that includes an upper end and a lower end with an opening on each of the upper end and the lower end, each opening being operable as an inlet or an outlet and configured to permit a fluid flow through the column, the column including an acoustic section being defined by an ensonified volume on one of the upper end or the lower end and a fluidized bed section that is separate from the acoustic section, the fluidized bed section including support structures dispersed in a fluid forming a fluidized bed in the fluidized bed section;
   an acoustic transducer at the acoustic section of the column and that generates an acoustic wave in the column in a direction transverse to a longitudinal axis of the column to form the ensonified volume; and
   the acoustic transducer being excited to generate the acoustic wave to form an edge effect across the column to block the support structures from passing through the acoustic wave and retain the support structures in the fluidized bed section of the column against fluid flow.

2. The system of claim 1, further comprising a mechanical agitator coupled to the column for agitating the fluid.

3. The system of claim 1, wherein the acoustic transducer is operated in one or more of a plurality of modes.

4. The system of claim 3, wherein the plurality of modes comprise a clustering mode and an edge effect mode.

5. The system of claim 1, wherein the acoustic transducer is configured to generate a multi-dimensional acoustic wave in the acoustic section of the column.

6. The system of claim 1, wherein the support structures further comprise mobile support structures bound to cellular material in the fluidized bed section of the column that are responsive to the acoustic wave.

7. The system of claim 6, wherein the mobile support structures comprise affinity beads with an affinity for the cellular material.

8. The system of claim 7, wherein the affinity beads comprise column packing in a range of from about 10% to about 30% of an entire column volume.

9. The system of claim 7, wherein the affinity beads comprise one or more of anti-TCR or anti-CD52 capturing antibodies.

10. The system of claim 7, wherein the affinity beads are configured as avidin-conjugated methacrylate beads.

11. A method for separating materials, comprising:
    providing support structures in a vertically oriented column for binding with a first material, wherein the column comprises:
    an upper end and a lower end with an opening on each of the upper end and the lower end, each opening being operable as an inlet or an outlet and configured to permit a fluid flow through the column;
    an acoustic section being defined by an ensonified volume on one of the upper end or the lower end and a fluidized bed section that is separate from the acoustic section, the fluidized bed section including support structures dispersed in a fluid forming a fluidized bed in the fluidized bed section; and
    an acoustic transducer at the acoustic section of the column and arranged to generate an acoustic wave in the column in a direction transverse to a longitudinal axis of the column to form the ensonified volume; and flowing a fluid mixture that includes the first material into the column; and generating an acoustic wave with the acoustic transducer in the acoustic section of the column to block the support structures from leaving the fluidized bed section of the column with the fluid flow.

12. The method of claim 11, further comprising agitating the fluid mixture in the column with a mechanical agitator.

13. The method of claim 11, further comprising generating the acoustic wave in one or more of a plurality of modes.

14. The method of claim 13, wherein the plurality of modes comprise a clustering mode and an edge effect mode.

15. The method of claim 11, further comprising generating a multi-dimensional acoustic wave in the acoustic section of the column.

16. The method of claim 11, wherein the support structures comprise affinity beads with an affinity for cellular material.

17. The method of claim 16, further comprising packing the column in a range of from about 10% to about 30% with the affinity beads of an entire column volume.

18. The method of claim 16, wherein the affinity beads comprise one or more of anti-TCR or anti-CD52 capturing antibodies.

19. The method of claim 16, wherein the affinity beads are configured as avidin-conjugated methacrylate beads.

20. An acoustic affinity separation method, comprising:
providing affinity beads in a fluidized bed section of a vertically oriented column, wherein the column comprises:
an upper end and a lower end with an opening on each of the upper end and the lower end, each opening being operable as an inlet or an outlet and configured to permit a fluid flow through the column;
an acoustic section being defined by an ensonified volume on one of the upper end or the lower end and a fluidized bed section that is separate from the acoustic section, the fluidized bed section including support structures dispersed in a fluid forming a fluidized bed in the fluidized bed section; and
an acoustic transducer at the acoustic section of the column and arranged to generate an coustic wave in the column in a direction transverse to a longitudinal axis of the column to form the ensonified volume;
generating an acoustic wave with the acoustic transducer in the acoustic section of the column;
flowing a cellular material fluid mixture in the column and through the acoustic wave;
configuring the acoustic wave to maintain the affinity beads in the fluidized bed section of the column and from passing through the acoustic wave.

* * * * *

UNITED STATES PATENT AND TRADEMARK OFFICE
CERTIFICATE OF CORRECTION

| | |
|---|---|
| PATENT NO. | : 11,459,540 B2 |
| APPLICATION NO. | : 15/983823 |
| DATED | : October 4, 2022 |
| INVENTOR(S) | : Rui Tostoes et al. |

It is certified that error appears in the above-identified patent and that said Letters Patent is hereby corrected as shown below:

On the Title Page

Line 25, in Related U.S. Application Data, item (63) delete "15/522,800" and insert -- 15/222,800 --

In the Claims

In Column [28], Line [7], in Claim [1] delete "oriented column oriented column" and insert
-- oriented column --

In Column [30], Line [17], in Claim [20] delete "an coustic" and insert -- an acoustic --

Signed and Sealed this
Fourteenth Day of March, 2023

Katherine Kelly Vidal
*Director of the United States Patent and Trademark Office*